(12) United States Patent
Voigt et al.

(10) Patent No.: US 6,407,041 B1
(45) Date of Patent: Jun. 18, 2002

(54) SUBSTITUTED 2,4-DIAMINO-1,3,5-TRIAZINES

(75) Inventors: Katharina Voigt, Monheim; Hans-Jochem Riebel, Selters; Stefan Lehr, Langenfeld; Andreas Lender, Wuppertal; Rolf Kirsten, Monheim, all of (DE); Markus Dollinger, Overland Park, KS (US); Mark Wilhelm Drewes, Langenfeld (DE); Ingo Wetcholowsky, Estancia Marambaia (BR); Yukiyoshi Watanabe, Oyama; Toshio Goto, Tochigi, both of (JP); Randy Allen Myers, Overland Park, KS (US)

(73) Assignees: Bayer Aktiengesellschaft, Leverkusen (DE); Nihon Bayer Agrochem, K.K., Tokyo (JP)

( * ) Notice: Subject to any disclaimer, the term of this patent is extended or adjusted under 35 U.S.C. 154(b) by 0 days.

(21) Appl. No.: 09/555,825

(22) PCT Filed: Nov. 28, 1998

(86) PCT No.: PCT/EP98/07691

§ 371 (c)(1),
(2), (4) Date: Jul. 10, 2000

(87) PCT Pub. No.: WO99/29677

PCT Pub. Date: Jun. 17, 1999

(30) Foreign Application Priority Data

Dec. 11, 1997 (DE) .......................... 197 55 016

(51) Int. Cl.$^7$ ................... C07D 251/18; C07D 251/50; C07D 251/52; A01N 43/70; A01N 43/68

(52) U.S. Cl. .................. 504/230; 544/206; 544/207; 544/208; 544/209; 504/232; 504/233; 504/234

(58) Field of Search .................. 504/230, 232, 504/233, 234; 544/206, 207, 208, 209

(56) References Cited

U.S. PATENT DOCUMENTS

| | | | |
|---|---|---|---|
| 3,816,419 A | * 6/1974 | Cross et al. | 260/249.9 |
| 3,932,167 A | * 1/1976 | Cross et al. | 71/93 |
| 4,742,060 A | 5/1988 | Shiokawa et al. | 514/252 |
| 4,845,106 A | 7/1989 | Shiokawa et al. | 514/342 |
| 5,021,431 A | 6/1991 | Buschauer et al. | 514/333 |
| 5,204,360 A | 4/1993 | Shiokawa et al. | 514/342 |
| 5,286,905 A | 2/1994 | Nakamura et al. | 564/234 |
| 5,290,754 A | 3/1994 | Nishii et al. | 504/232 |
| 5,298,507 A | 3/1994 | Shiokawa et al. | 514/256 |
| 5,403,815 A | 4/1995 | Nishii et al. | 504/230 |
| 5,248,032 A | 6/1995 | Shiokawa et al. | 514/226.8 |
| 5,461,167 A | 10/1995 | Shiokawa et al. | 548/202 |
| 5,580,889 A | 12/1996 | Shiokawa et al. | 514/343 |
| 5,583,259 A | 12/1996 | Brown et al. | 564/346 |
| 5,750,704 A | 5/1998 | Shiokawa et al. | 546/275.1 |
| 6,022,967 A | 2/2000 | Shiokawa et al. | 544/298 |

OTHER PUBLICATIONS

J. Org. Chem. 34 (month unavailabel) 1969, pp. 466–468, F.I. Carroll, The Preparation and Reduction of 2–Mehtyl–2–nitro–3–benzylthiopropanol.

J. Heterocycl. Chem. Dec. 11, 1974, pp. 985–989, Cignarella et al, Synthesis and Configuration Of trans–1–Amino–4–benzyl–2,6–dimethylpiperazine as an Intermediate of Semi–synthetic Rifamycins.

Liebigs Ann. Chem. (month unavailable) 1980, pp. 786–790, Synthesis of Isomeric N–Benzyl Derivatives of 1,2–Propanediamine, Kurganov et al.

Can. J. Chem. 60 (month unavailable) 1982, McArthur et al, pp. 1836–1841, Polymer supported Enantioselective reactions, 11 α–Methylation of cyclohexanone.

Tetrahedron, vol. 40, No. 8 (month unavailable) 1984, pp. 1255–1268, Ojima et al, Synthesis Of Chiral Oligopeptides by Means of Catalytic Asymmetric Hydrogenation of Dehydropeptides.

J. Am. Chem. Soc. 110, (month unavailable) 1988, pp. 3826–3869, Bjørnholm et al, Distonic Ions as Reacting Species.

J. Am. Chem. Soc. 109, (month unavailable) 1987, pp. 236–239, Lubell et al, Configurational Stability of N–Protected α–Amino Aldehydes.

Tetrahedron Lett., 30, (month unavailable) 1989, pp. 731–734, Kamimura et al, Diastereoselective Preparation of Anti–βAmino Alcohols Via Michael Addition of Alkoxide Anions to Nitroolefins and Subsequent Hydrogenation Reaction.

Tetrahedron Asymmetry, vol. 3, No. 5, (month unavailable) 1992, pp. 587–590, Touet et al Asymmetric Michael Additions of Grignard Reagents to Cinnamamides Deriving from N–Alkyl (R)–(–)–2–Aminobutan–1–OL.

Tetrahedron: Asymmetry, vol. 7, Nor. 12, (month unavailable) 1996, pp. 3397–3406, Ince et al, Synthesis of Chiral, Nonracemic Methyleneaziridines Derived From β–amino Alcohols.

(List continued on next page.)

*Primary Examiner*—John M. Ford
(74) *Attorney, Agent, or Firm*—Joseph C. Gil

(57) ABSTRACT

The invention relaters to compounds of the formula:

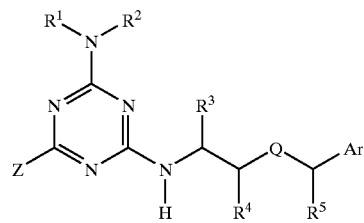

and their use as herbicides.

5 Claims, No Drawings

OTHER PUBLICATIONS

Tetrahedrons Lett., vol. 34, No. 18, (month unavailable) 1993, pp. 2957–2960, Touet et al, O–Benzyl Derivatives of (S)–(+) and (R)–(–)–2–Aminobutan–1–ol as New Resolving Agents for Racemic Acids Practical Resolutions of N–Acyl Derivatives of Phenyglycine and 4–Hydroxyphenylglycine.

Tetrahedron, vol. 51, No. 6 (month unavailable) 1995, pp. 1709–1720, Toute et al, Agents de Dédoublement. 3. Ethers Benzyliques du (R)–(–) et du (S)–(+)–2–Aminobutan–1–ol, et leur Utilisation dans le Dédoublement de Dérivés N–Acylés de la Phénylglycine et de la p–Hydroxyphénylglycine.

J. Org. Chem. (month unavailable) 1996, 61, pp. 7285–7290, Chinchilla et al, Determination of the Absolute Configuration of Amines and α–Amino Acids by H NMR of (R)–O–Aryllactic Acid Amides.

Tetrahedron, vol. 52, No. 12, (month unavailable) 1996, pp. 4199–4214, Occhiato et al, Probing Enzyme Stereospecificity. Inhibition of α–Chymotrypsin and Subtilisin Carlsberg by Chiral Amine–and Aminoalcohol–Derivatives.

* cited by examiner

SUBSTITUTED 2,4-DIAMINO-1,3,5-TRIAZINES

TECHNICAL FIELD OF THE INVENTION

The invention relates to novel substituted 2,4-diamino-1,3,5-triazines, to processes and novel intermediates for their preparation and to their use as herbicides.

BACKGROUND OF THE INVENTION

A number of substituted aryloxyalkylaminotriazines is already known from the (patent) literature (cf. EP-273 328, EP-411 153/WO 90/09378). However, these compounds have hitherto not obtained any particular significance.

DETAILED DESCRIPTION OF THE INVENTION

This invention now provides the novel substituted 2,4-diamino-1,3,5-triazines of the general formula (I)

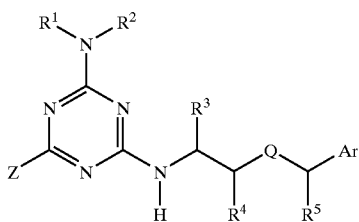
(I)

in which
  Q represents O (oxygen), S (sulphur), SO, SO$_2$, NH or N(alkyl),
  $R^1$ represents hydrogen or represents optionally substituted alkyl,
  $R^2$ represents hydrogen, represents formyl or represents in each case optionally substituted alkyl, alkylcarbonyl, alkoxycarbonyl or alkylaminocarbonyl,
  $R^3$ represents in each case optionally substituted alkyl or cycloalkyl,
  $R^4$ represents hydrogen or alkyl,
  $R^5$ represents hydrogen or alkyl,
  Ar represents in each case optionally substituted aryl or heteroaryl, and
  Z represents hydrogen, cyano, halogen, or represents in each case optionally substituted alkyl, alkoxy, alkylcarbonyl, alkoxycarbonyl, alkylthio, alkylsulphinyl, alkylsulphonyl, alkenyl, alkinyl or cycloalkyl.

The novel substituted 2,4-diaminotriazines of the general formula (I) are obtained when
  (a) biguanides of the general formula (II)

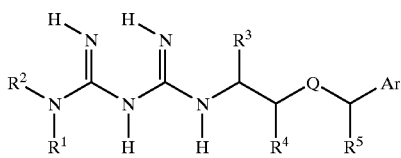
(II)

in which
  Q, $R^1$, $R^2$, $R^3$, $R^4$, $R^5$ and Ar are as defined above and/or acid adducts of compounds of the general formula (II)

are reacted with alkoxycarbonyl compounds of the general formula (III)

Z—CO—OR' (III)

in which
  Z is as defined above and
  R' represents alkyl,
if appropriate in the presence of a reaction auxiliary and if appropriate in the presence of a diluent,
or when
  (b) substituted halogenotriazines of the general formula (IV)

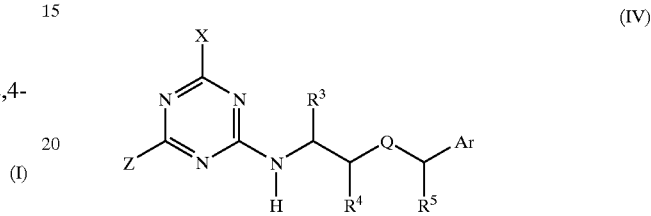
(IV)

in which
  Q, $R^3$, $R^4$, $R^5$, Ar and Z are as defined above and
  X represents halogen,
are reacted with nitrogen compounds of the general formula (V)

(V)

in which
  $R^1$ and $R^2$ are as defined above,
if appropriate in the presence of a reaction auxiliary and if appropriate in the presence of a diluent,
or when
  (c) substituted aminotriazines of the general formula (VI)

(VI)

in which
  $R^1$, $R^2$ and Z are as defined above and
  $Y^1$ represents halogen or alkoxy,
are reacted with substituted alkyl amines of the general formula (VII)

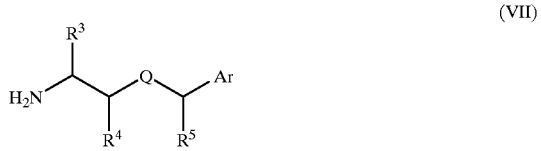
(VII)

in which
  Q, Ar, $R^3$, $R^4$ and $R^5$ are as defined above, if appropriate in the presence of a reaction auxiliary and if appropriate in the presence of a diluent,
or when
(d) substituted 2,4-diamino-1,3,5-triazines of the general formula (Ia)

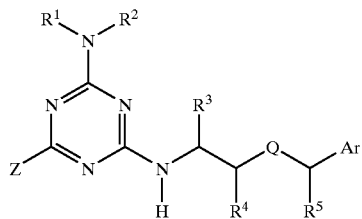

in which
Q, $R^1$, $R^3$, $R^4$, $R^5$, Ar and Z are as defined above
are reacted with alkylating or acylating agents of the general formula (VIII)

$$Y^2\text{—}R^2 \qquad (VIII)$$

in which
$R^2$ is as defined above, except for hydrogen, and
$Y^2$ represents halogen, —O—$R^2$ or —O—CO—$R^2$,
if appropriate in the presence of a reaction auxiliary and if appropriate in the presence of a diluent,
and further conversions within the scope of the above definition of substituents are carried out by customary methods on the compounds of the general formula (I) obtained by the processes described under (a), (b), (c) or (d).

The novel substituted 2,4-diamino-1,3,5-triazines of the general formula (I) have strong and selective herbicidal activity.

The compounds of the general formula (I) according to the invention contain at least one asymmetrically substituted carbon atom and can therefore be present in different enantiomeric (R- and S-configured forms) and/or diasteromeric forms. The invention relates both to the various possible individual enantiomeric or stereoisomeric forms of the compounds of the general formula (I) and to the mixtures of these isomeric compounds.

In the definitions, the hydrocarbon chains, such as alkyl—including in combination with heteroatoms, such as in alkoxy or alkylthio—are in each case straight-chain or branched. Halogen generally represents fluorine, chlorine, bromine or iodine, preferably fluorine, chlorine or bromine, in particular fluorine or chlorine.

The invention preferably provides compounds of the formula (I) in which
Q represents O (oxygen), S (sulphur), SO, $SO_2$, NH or N($C_1$–$C_4$-alkyl),
$R^1$ represents hydrogen or represents optionally hydroxyl-, cyano-, halogen- or $C_1$–$C_4$-alkoxy-substituted alkyl having 1 to 6 carbon atoms,
$R^2$ represents hydrogen, represents formyl or represents in each case optionally cyano-, halogen- or $C_1$–$C_4$-alkoxy-substituted alkyl, alkylcarbonyl, alkoxycarbonyl or alkylaminocarbonyl having in each case 1 to 6 carbon atoms in the alkyl groups,
$R^3$ represents optionally hydroxyl-, cyano-, halogen- or $C_1$–$C_4$-alkoxy-substituted alkyl having 1 to 6 carbon atoms or represents optionally cyano-, halogen- or $C_1$–$C_4$-alkyl-substituted cycloalkyl having 3 to 6 carbon atoms,
$R^4$ represents hydrogen or alkyl having 1 to 4 carbon atoms,
$R^5$ represents hydrogen or alkyl having 1 to 4 carbon atoms,
Ar represents in each case optionally substituted phenyl, naphthyl, tetralinyl or heteroaryl,
where the possible heteroaryl groupings are preferably selected from the following group:
furyl, benzofuryl, thienyl, benzothienyl, thiazolyl, benzothiazolyl, oxazolyl, benzoxazolyl, isoxazolyl, thiadiazolyl, oxadiazolyl, pyrazolyl, imidazolyl, pyrrolyl, pyridinyl, pyrimidinyl,
and where the possible substituents are in each case selected from the following group:
hydroxyl, cyano, carbamoyl, thiocarbamoyl, nitro, halogen, in each case optionally hydroxyl-, cyano- or halogen-substituted alkyl or alkoxy having in each case 1 to 6 carbon atoms, in each case optionally halogen-substituted alkylcarbonyl, alkoxycarbonyl, alkylthio, alkylsulphinyl, alkylsulphonyl, dialkylamino, alkylcarbonylamino, alkylsulphonylamino, bis-alkylcarbonyl-amino, bis-alkylsulphonyl-amino, N-alkyl-N-alkylcarbonyl-amino or N-alkyl-N-alkylsulphonyl-amino having in each case 1 to 6 carbon atoms in the alkyl groups, in each case optionally hydroxyl-, cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or phenoxy, and in each case optionally halogen-substituted methylenedioxy or ethylenedioxy, and
Z represents hydrogen, cyano, halogen, represents in each case optionally hydroxyl-, cyano-, halogen-, $C_1$–$C_4$-alkoxy-, $C_1$–$C_4$-alkyl-carbonyl-, $C_1$–$C_4$-alkoxy-carbonyl-, $C_1$–$C_4$-alkylthio-, $C_1$–$C_4$-alkylsulphinyl- or $C_1$–$C_4$-alkylsulphonyl-substituted alkyl, alkoxy, alkylcarbonyl, alkoxycarbonyl, alkylthio, alkylsulphinyl or alkylsulphonyl having in each case 1 to 6 carbon atoms in the alkyl groups, represents in each case optionally cyano-, halogen- or $C_1$–$C_4$-alkoxy-substituted alkenyl or alkinyl having in each case 2 to 4 carbon atoms in the alkenyl or alkinyl groups, or represents optionally cyano-, halogen- or $C_1$–$C_4$-alkyl-substituted cycloalkyl having 3 to 6 carbon atoms.

From among the compounds of the general formula (I) defined above as being preferred ("preferably"), particular emphasis is given to the following groups:
(A) the compounds of the formula (I) in which Q, $R^1$, $R^2$, $R^3$, $R^4$, $R^5$ and Z are as defined above and Ar represents in each case optionally substituted phenyl or naphthyl, where the possible substituents are as defined above;
(B) the compounds of the formula (I) in which Q, $R^1$, $R^2$, $R^3$, $R^4$, $R^5$ and Z are as defined above and Ar represents optionally substituted heterocyclyl, where the possible heterocyclyl groupings and the possible substituents are as defined above.

The invention relates in particular to compounds of the formula (I) in which
Q represents O (oxygen), S (sulphur) or NH,
$R^1$ represents hydrogen or represents in each case optionally hydroxyl-, cyano-, fluorine-, chlorine-, methoxy- or ethoxy-substituted methyl, ethyl, n- or i-propyl, n-, i-, s- or t-butyl,
$R^2$ represents hydrogen, represents formyl, or represents in each case optionally cyano-, fluorine-, chlorine-, bromine-, methoxy- or ethoxy-substituted methyl, ethyl, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, $R^3$ represents in each case optionally hydroxyl-, cyano-, fluorine-, chlorine-, methoxy- or ethoxy-substituted ethyl, n- or i-propyl, n-, i-, s- or t-butyl or represents in each case optionally cyano-, fluorine-, chlorine-, methyl- or ethyl-substituted cyclopropyl, cyclobutyl, cyclopentyl or cyclohexyl, $R^4$ represents hydrogen or methyl, $R^5$ represents hydrogen or methyl, Ar represents in each case optionally substituted phenyl, naphthyl, tetralinyl or heteroaryl,
where the possible heteroaryl groupings are selected from the following group:
furyl, benzofuryl, thienyl, benzothienyl, thiazolyl, benzothiazolyl, oxazolyl, benzoxazolyl, isoxazolyl, thiadiazolyl, oxadiazolyl, pyrazolyl, imidazolyl, pyrrolyl, pyridinyl, pyrimidinyl,
and where the possible substituents are in each case preferably selected from the following group:
hydroxyl, cyano, carbamoyl, thiocarbamoyl, nitro, fluorine, chlorine, bromine, in each case optionally hydroxyl-, cyano-, fluorine- or chlorine-substituted methyl, ethyl, n- or i-propyl, n-, i-, s- or t-butyl, methoxy, ethoxy, n- or i-propoxy, n-, i-, s- or t-butoxy, in each case optionally fluorine- or chlorine-substituted acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, dimethylamino, diethylamino, acetylamino, propionylamino, methylsulphonylamino, ethylsulphonylamino, bis-acetyl-amino, bis-methylsulphonyl-amino, N-methyl-N-acetyl-amino or N-methyl-N-methylsulphonylamino, in each case optionally hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl or phenoxy, and in each case optionally fluorine- or chlorine-substituted methylenedioxy or ethylenedioxy, and Z represents fluorine, chlorine, bromine, represents in each case optionally hydroxyl-, cyano-, nitro-, fluorine-, chlorine-, methoxy-, ethoxy-, n- or i-propoxy-, n-, i-, s- or t-butoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl, represents in each case optionally cyano-, fluorine-, chlorine-, bromine-, methoxy- or ethoxy-substituted ethenyl, propenyl, butenyl, ethinyl, propinyl or butinyl, or represents in each case optionally cyano-, fluorine-, chlorine-, methyl- or ethyl-substituted cyclopropyl, cyclobutyl, cyclopentyl or cyclohexyl.

From among the compounds of the formula (I) defined above as being particularly preferred, particular emphasis is given to the following groups:

(A') the compounds of the formula (1) in which $R^1$, $R^2$, $R^3$, $R^4$, $R^5$ and Z are as defined above, Q represents O (oxygen) and Ar represents in each case optionally substituted phenyl or naphthyl, where the possible substituents are as defined above, with the proviso that the substituents of the carbon atom to which $R^3$ is attached are arranged in the R configuration;

(B') the compounds of the formula (I) in which $R^1$, $R^2$, $R^3$, $R^4$, $R^5$ and Z are as defined above, Q represents O (oxygen) and Ar represents in each case optionally substituted phenyl or naphthyl, where the possible substitutents are as defined above, with the proviso that the substituents of the carbon atoms to which $R^3$ is attached are arranged in the S configuration.

The abovementioned general or preferred radical definitions apply both to the end products of the formula (I) and correspondingly to the starting materials or intermediates required in each case for the preparation. These radical definitions can be combined with one another at will, i.e. including combinations between the given preferred ranges.

Examples of the compounds of the formula (I) according to the invention are listed in the groups below. Here, the general formulae represent in each case the R enantiomers, the S enantiomers and the racemates.

Group 1

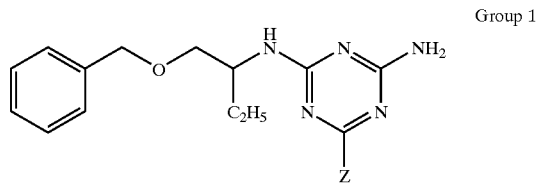

Here, Z has, for example, the meanings given in the list below:

methyl, ethyl, n- oder i-propyl, n-, i-, s- or t-butyl, fluoromethyl, difluoromethyl, trifluoromethyl, chloromethyl, dichloromethyl, chlorofluoromethyl, chlorobromomethyl, chlorodifluoromethyl, fluorodichloromethyl, bromo-difluoromethyl, trichloromethyl, 1-fluoroethyl, 2-fluoro-ethyl, 1-chloro-ethyl, 2-chloro-ethyl, 1-bromo-ethyl, 1-chloro-1-fluoro-ethyl, 1-fluoro-propyl, 2-fluoro-propyl, 3-fluoro-propyl, 1-chloro-propyl, 2-chloro-propyl, 3-chloro-propyl, 1-bromo-propyl, 1-fluoro-1-methyl-ethyl, 2-fluoro-1-methyl-ethyl, 1-chloro-1-methyl-ethyl, 1-fluoro-1-methyl-propyl, 1-chloro-1-ethyl-propyl, 1-fluoro-1-ethyl-propyl, 1-fluoro-2-methyl-propyl, 1-chloro-2-methyl-propyl, 2-chloro- -methyl-ethyl, 1,1-difluoro-ethyl, 1,2-difluoro-ethyl, 1,1-dichloro-ethyl, 2,2,2-trifluoro-ethyl, 1,2,2,2-tetrafluoro-ethyl, perfluoroethyl, 1,1-difluoro-propyl, 1,1-dichloro-propyl, perfluoropropyl, 1-fluoro-butyl, 1-chloro-butyl, perfluorobutyl, perfluoropentyl, perfluorohexyl, 1-hydroxy-ethyl, 1-hydroxy-1-methyl-ethyl, 1-hydroxy-propyl, methoxymethyl, ethoxymethyl, dimethoxy-methyl, 1-methoxyethyl, 2-methoxy-ethyl, 1,1-dimethoxy-ethyl, 1-ethoxy-ethyl, 2-ethoxy-ethyl, 2,2-dimethoxy-ethyl, 2,2-diethoxy-ethyl, 2-methoxy-1-methyl-ethyl, 2-methoxy-1-ethyl-ethyl, 2-ethoxy-1-methyl-ethyl, 2-ethoxy-1-ethyl-ethyl, 2,2-bis-methoxy-methyl, methylthiomethyl, ethylthiomethyl, 1-methylthio-ethyl, 2-methylthioethyl, 1-ethylthio-ethyl, 2-ethylthioethyl, methylsulphinylmethyl, ethylsulphinylmethyl, methylsulphonylmethyl, ethylsulphonylmethyl, vinyl, 1-chloro-vinyl, 2-chloro-vinyl, 1-fluoro-vinyl, 2-fluoro-vinyl, 1-bromo-vinyl, 2-bromo-vinyl, 1,2-dichloro-vinyl, 1,2-dibromo-vinyl, 1,2-difluoro-vinyl, 2,2-dichloro-vinyl, 2,2-difluoro-vinyl, 2,2-dibromo-vinyl, 1-chloro-2-fluoro-vinyl, 1-fluoro-2-chloro-vinyl, 2-bromo-1-chloro-vinyl, 2-bromo-2-chloro-vinyl, 1-bromo-2-fluoro-vinyl, 1-fluoro-2-bromo-vinyl, 1-bromo-2-chloro-vinyl, trichlorovinyl, trifluorovinyl, tribromovinyl, 1-fluoro-2,2-dichloro-vinyl, 1-bromo-2,2-dichloro-vinyl, 1-fluoro-2,2-dibromo-vinyl, 1-chloro-2,2-difluoro-vinyl, 1-chloro-2,2-dibromo-vinyl, 1-bromo-2,2-difluoro-vinyl, 2-fluoro-1,2-dichloro-vinyl, 2-chloro-1,2-difluoro-vinyl, 2-bromo-1,2-difluoro-vinyl, 2-bromo-1,2-dichloro-vinyl, 2-chloro-1,2-dibromo-vinyl, 2-fluoro-1,2-dibromo-vinyl, 2-bromo-1-chloro-2-fluoro-vinyl, 2-methoxy-vinyl, 2-ethoxyvinyl, allyl, 2-chloro-allyl, 3-chloro-allyl, 3,3-dichloro-allyl, propen-1-yl, propen-2-yl, 1-chloro-propen-1-yl, 1-bromo-propen-1-yl, 1-fluoro-propen-2-yl, 1-chloro-propen-2-yl, 1-bromo-propen-2-yl, 2-methoxy-propen-1-yl, 2-ethoxy-propen-1-yl, 3,3,3-trifluoro-propen-1-yl, 3,3,3-trifluoro-propen-2-yl, 1-chloro-propen-2-yl, 1-fluoro-propen-2-yl, 1-bromo-propen-2-yl, 1,2-dichloro-propen-1-yl, 1,2-dibromo-propen-1-yl, 1,2-difluoro-propen-1-yl, 1,1-dichloro-propen-2-yl, 1,1-dibromo-propen-2-yl, 1,1-difluoro-propen-2-yl, 1-chloro-2-fluoro-propen-1-yl, 1-chloro-2-bromo-propen-1-yl, 1-bromo-2-chloro-propen-1-yl, 1-bromo-2-fluoro-propen-1-yl, 1-chloro-3,3,3-trifluoro-propen-2-yl, 1-bromo-3,3,3-trifluoro-propen-2-yl, 1-fluoro-3,3,3-trichloro-propen-1-yl, 1,3,3,3-tetrafluoro-propen-1-yl, 1,3,3,3-tetrafluoro-propen-2-yl, 1-bromo-2-chloro-3,3,3-trifluoro-propen-1-yl, 1,1,3,3,3-pentafluoro-propen-1-yl, 1,2,3,3,3-pentafluoro-propen-1-yl, 1,1-dichloro-3,3,3-trifluoro-propen-2-yl, 1,2-dichloro-3,3,3-trifluoro-propen-2-yl, 1,1-dibromo-3,3,3-trifluoro-propen-2-yl, 1,2-dibromo-3,3,3-trifluoro-propen-2-yl, 1-chloro-2,3,3,3-tetrafluoro-1-propen-1-yl, 2-methyl-propen-1-yl, 1-chloro-2-methyl-propen-1-yl, 1-bromo-2-methyl-propen-1-yl, 1-fluoro-2-methyl-propen-1-yl, 1-bromo-2-methyl-3,3,3-trifluoro-propen-1-yl, 1-chloro-3,3,3-trifluoro-2-trifluoromethyl-propen-1-yl, 1-bromo-3,3,3-trifluoro-2-trifluoromethyl-propen-1-yl, 1-chloro-3,3,3-trifluoro-propen-1-yl, 1-bromo-3,3,3-trifluoro-propen-1-yl, 1-chloro-2,3,3,3-tetrafluoro-propen-1-yl, 1-chloro-2-bromo-3,3,3-trifluoro-propen-1-yl, 1-chloro-2-methyl-3,3,3-trifluoro-propen-1-yl, 1-bromo-2-fluoro-propen-1-yl, 1-buten-1-yl, 1-buten-2-yl, 2-buten-1-yl, 2-buten-2-yl, 1-chloro-1-buten-1-yl, 1-bromo-1-buten-1-yl, 1-fluoro-1-buten-1-yl, 1-chloro-1-buten-2-yl, 1-fluoro-1-buten-2-yl, 1-bromo-1-buten-2-yl, 1,2-difluoro-1-buten-1-yl, 1,2-dichloro-1-buten-1-yl, 1,2-dibromo-1-buten-1-yl, 1-bromo-2-fluoro-1-buten-1-yl, 3-methyl-2-buten-2-yl, 1-chloro-2-fluoro-1-buten-1-yl, 1-bromo-2-chloro-1-buten-1-yl, 1,1,1-trifluoro-2-methyl-2-buten-2-yl, 4,4,4-trifluoro-2-methyl-buten-2-yl, 4,4,4-trifluoro-3-trifluoromethyl-2-buten-2-yl, 1-chloro-2-methyl-3,3,3-trifluoro-propen-1-yl, 3-chloro-2-buten-2-yl, 3-bromo-2-buten-2-yl, 3-fluoro-2-buten-2-yl, 1-chloro-2-methyl-1-buten-1-yl, 1-bromo-2-methyl-1-buten-1-yl, 1-fluoro-2-methyl-1-buten-1-yl, 1-fluoro-3-methyl-1-buten-1-yl, 1-chloro-3-methyl-1-buten-1-yl, 2-methoxy-1-buten-1-yl, 2-ethoxy-1-buten-1-yl, 1,1-dichloro-1-buten-2-yl, 1,1-dibromo-1-buten-2-yl, 1,1-difluoro-1-buten-2-yl, 1-chloro-2-fluoro-1-buten-1-yl, 1-chloro-2-bromo-1-buten-1-yl, 1-chloro-2-trifluoromethyl-1-buten-1-yl, 1,1,1-trifluoro-2-buten-2-yl, 4,4,4-trifluoro-2-buten-2-yl, 4,4,4-trifluoro-3-methyl-2-buten-2-yl, 1,1,1-trifluoro-3-methyl-2-penten-2-yl, 1,1,1-trifluoro-3-ethyl-2-penten-2-yl, 1,1,1,4,4,4-hexafluoro-2-buten-2-yl, 1-chloro-2-ethyl-1-buten-1-yl, 1-bromo-2-ethyl-1-buten-1-yl, 1-fluoro-2-ethyl-1-buten-1-yl, 2-penten-2-yl, 2-penten-3-yl, 2-chloro-2-penten-3-yl, 2-bromo-2-penten-3-yl, 2-fluoro-2-penten-3-yl, 3-chloro-2-penten-2-yl, 3-bromo-2-penten-2-yl, 3-fluoro-2-penten-2-yl, 3-trifluoromethyl-2-penten-2-yl, 1,1,1-trifluoro-2-penten-3-yl, 1,1,1-trifluoro-2-penten-2-yl, 1,1,1-trifluoro-3-methyl-2-penten-2-yl, 2-methyl-3-yl 2-penten-3-yl, 3-methyl-2-penten-2-yl, 1,1,1-trifluoro-2-trifluoromethyl-2-penten-3-yl, 4-methyl-3-hexen-3-yl, 4-fluoro-3-hexen-3-yl, 4-chloro-3-hexen-3-yl, 4-bromo-3-hexen-3-yl, 1,1,1-trifluoro-2-methyl-2-hexen-3-yl, 4-ethyl-3-hexen-3-yl, ethinyl, 2-chloro-ethinyl, 2-bromo-ethinyl, propin-1-yl, propin-3-yl, 3,3,3-trifluoro-propin-1-yl, 1-butin-1-yl, 1-butin-3-yl, 3-methyl-1-butin-1-yl, 1-pentin-1-yl, cyclopropyl, 1-cyano-cyclopropyl, 1-fluoro-cyclopropyl, 1-chloro-cyclopropyl, 2-cyano-cyclopropyl, 2-fluorocyclopropyl, 2-chloro-cyclopropyl, 2,2-difluoro-cyclopropyl, 2,2-dichloro-cyclopropyl, cyclobutyl, 2,2-difluoro-cyclobutyl, 2,2,3-trifluoro-cyclobutyl, 2,2-difluoro-3-chloro-cyclobutyl, cyclopentyl, cyclohexyl.

Group 2

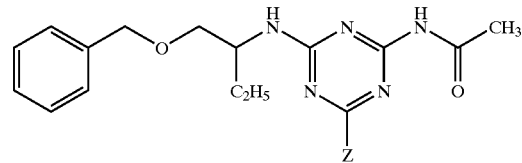

Here, Z has, for example, the meanings given above in group 1.

Group 3

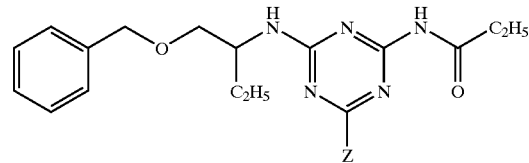

Here, Z has, for example, the meanings given above in group 1.

Group 4

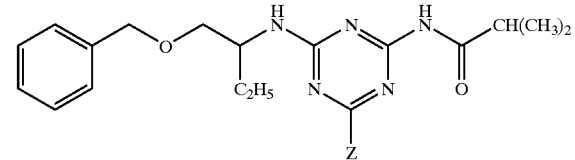

Here, Z has, for example, the meanings given above in group 1.

Group 5

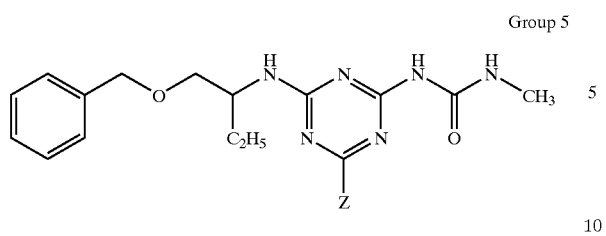

Here, Z has, for example, the meanings given above in group 1.

Group 6

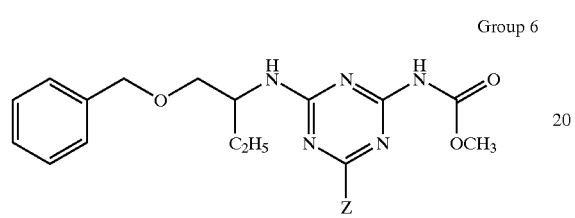

Here, Z has, for example, the meanings given above in group 1.

Group 7

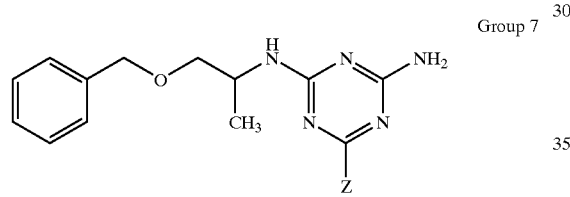

Here, Z has, for example, the meanings given above in group 1.

Group 8

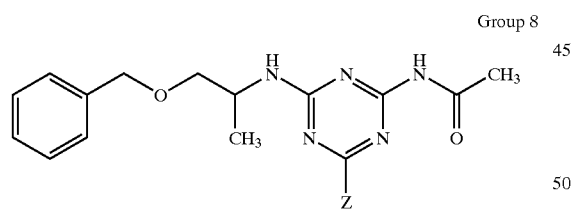

Here, Z has, for example, the meanings given above in group 1.

Group 9

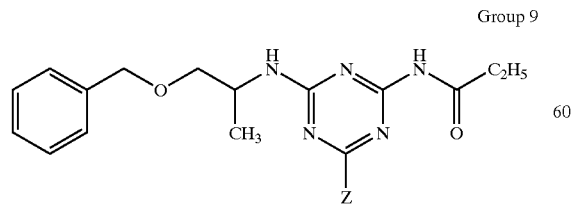

Here, Z has, for example, the meanings given above in group 1.

Group 10

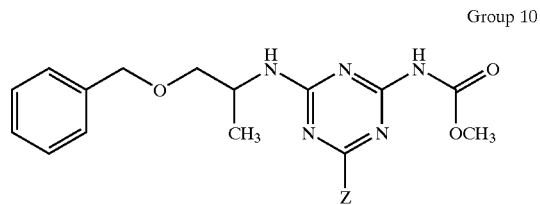

Here, Z has, for example, the meanings given above in group 1.

Group 11

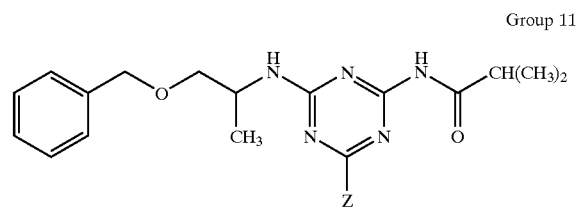

Here, Z has, for example, the meanings given above in group 1.

Group 12

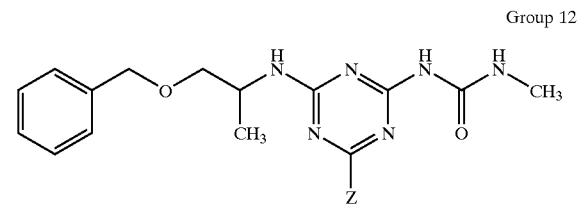

Here, Z has, for example, the meanings given above in group 1.

Group 13

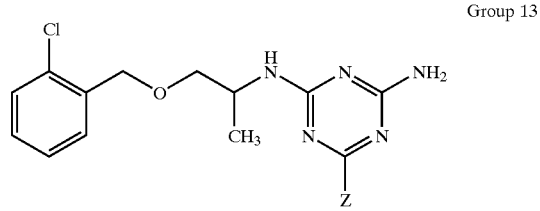

Here, Z has, for example, the meanings given above in group 1.

Group 14

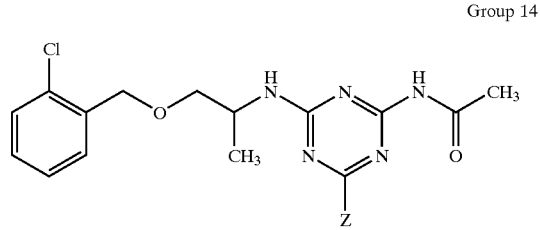

Here, Z has, for example, the meanings given above in group 1.

Group 15

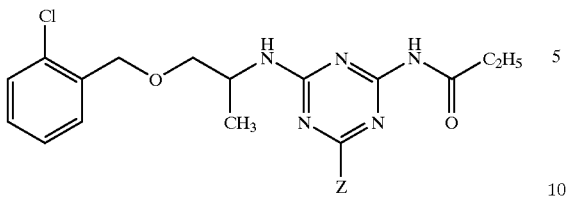

Here, Z has, for example, the meanings given above in group 1.

Group 16

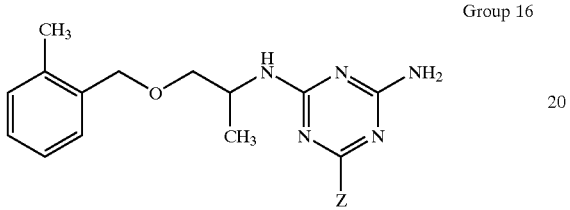

Here, Z has, for example, the meanings given above in group 1.

Group 17

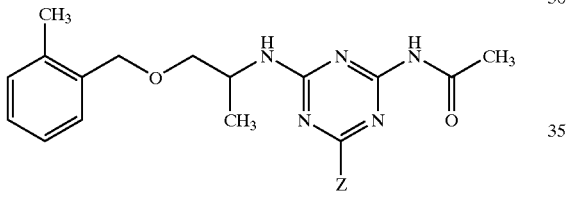

Here, Z has, for example, the meanings given above in group 1.

Group 18

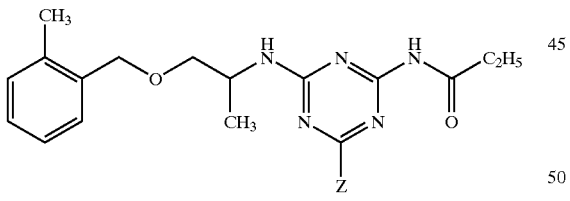

Here, Z has, for example, the meanings given above in group 1.

Group 19

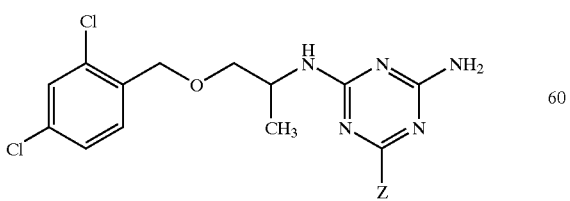

Here, Z has, for example, the meanings given above in group 1.

Group 20

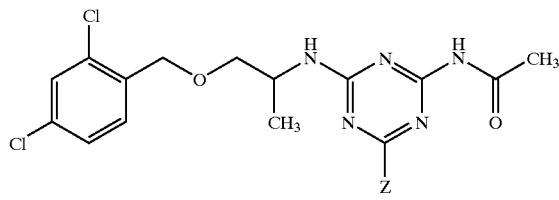

Here, Z has, for example, the meanings given above in group 1.

Group 21

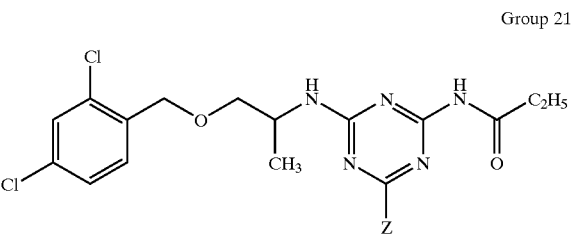

Here, Z has, for example, the meanings given above in group 1.

Group 22

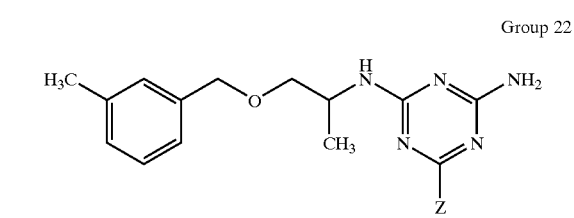

Here, Z has, for example, the meanings given above in group 1.

Group 23

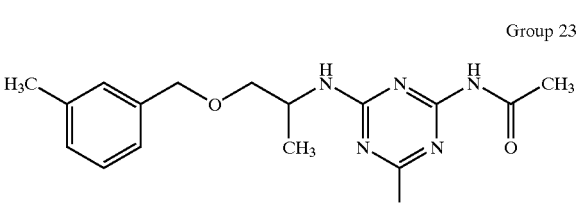

Here, Z has, for example, the meanings given above in group 1.

Group 24

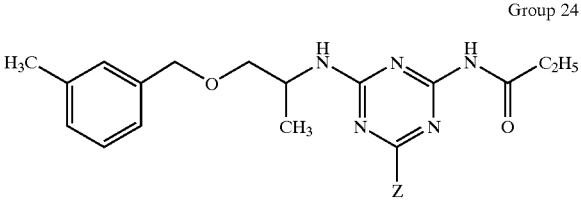

Here, Z has, for example, the meanings given above in group 1.

Group 25

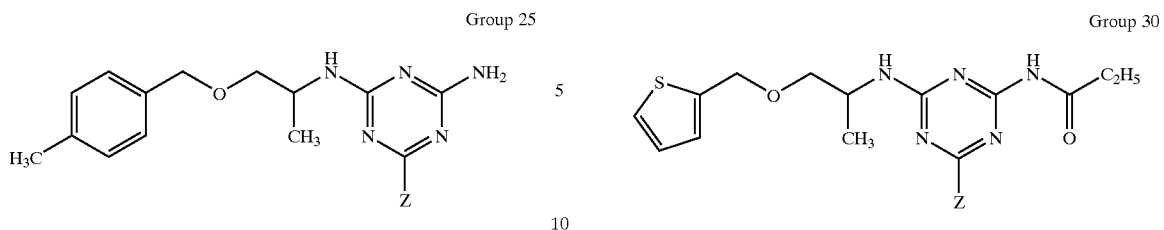

Here, Z has, for example, the meanings given above in group 1.

Group 26

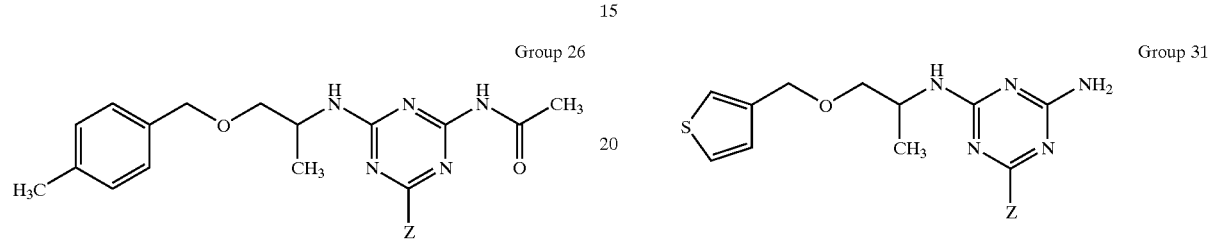

Here, Z has, for example, the meanings given above in group 1.

Group 27

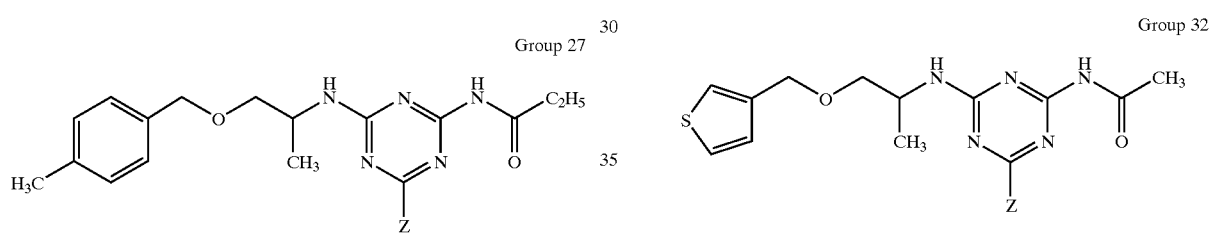

Here, Z has, for example, the meanings given above in group 1.

Group 28

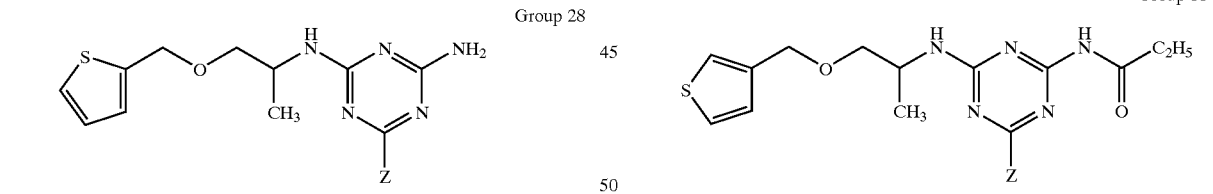

Here, Z has, for example, the meanings given above in group 1.

Group 29

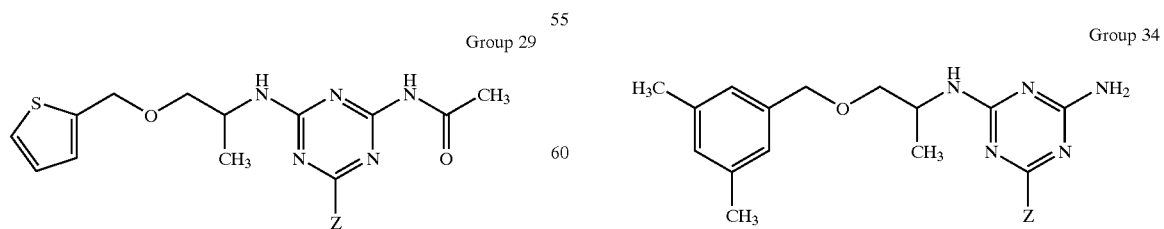

Here, Z has, for example, the meanings given above in group 1.

Group 30

Here, Z has, for example, the meanings given above in group 1.

Group 31

Here, Z has, for example, the meanings given above in group 1.

Group 32

Here, Z has, for example, the meanings given above in group 1.

Group 33

Here, Z has, for example, the meanings given above in group 1.

Group 34

Here, Z has, for example, the meanings given above in group 1.

Group 35

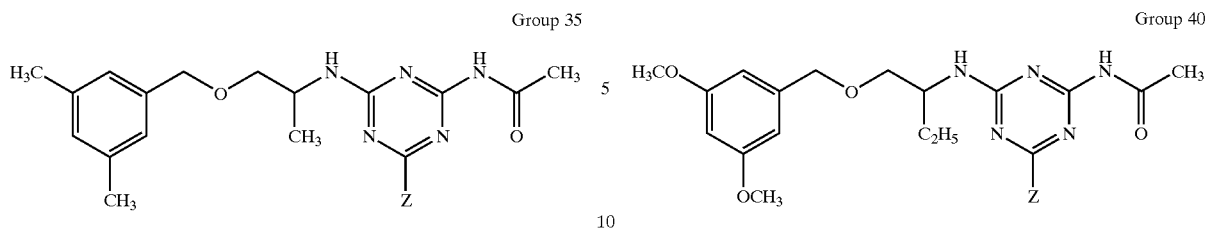

Here, Z has, for example, the meanings given above in group 1.

Group 36

Here, Z has, for example, the meanings given above in group 1.

Group 37

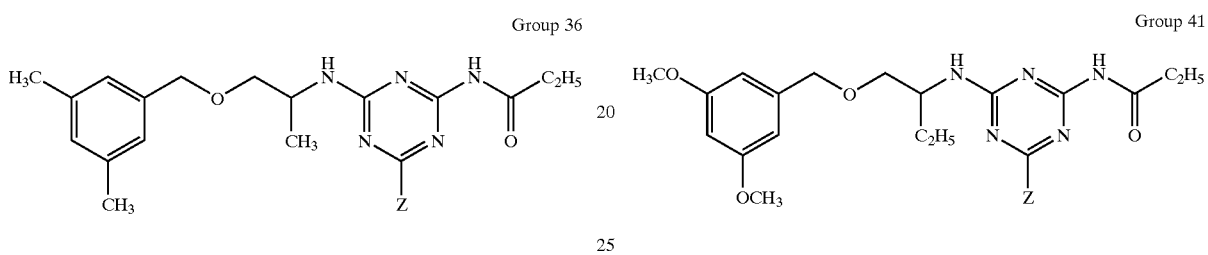

Here, Z has, for example, the meanings given above in group 1.

Group 38

Here, Z has, for example, the meanings given above in group 1.

Group 39

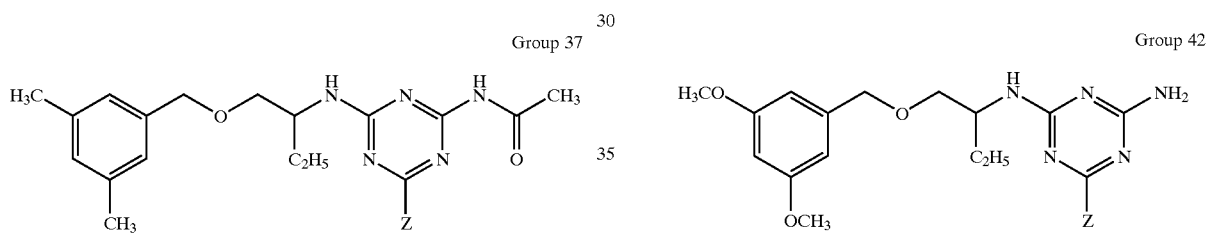

Here, Z has, for example, the meanings given above in group 1.

Group 40

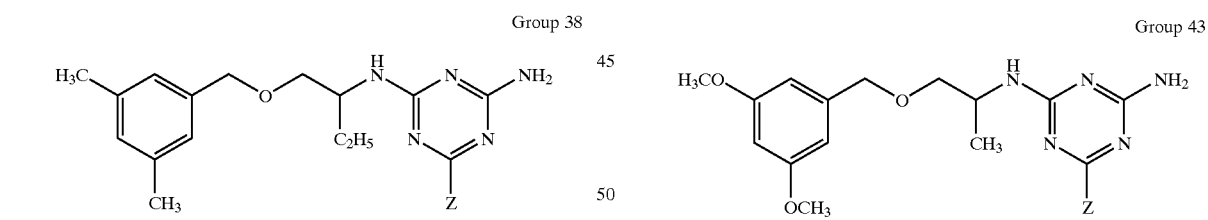

Here, Z has, for example, the meanings given above in group 1.

Group 41

Here, Z has, for example, the meanings given above in group 1.

Group 42

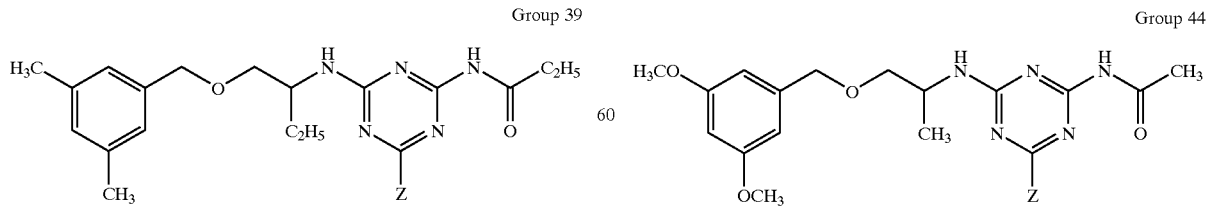

Here, Z has, for example, the meanings given above in group 1.

Group 43

Here, Z has, for example, the meanings given above in group 1.

Group 44

Here, Z has, for example, the meanings given above in group 1.

Group 45

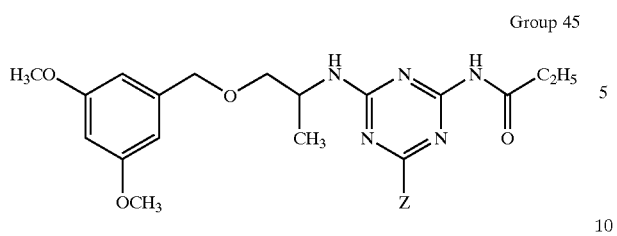

Here, Z has, for example, the meanings given above in group 1.

Group 46

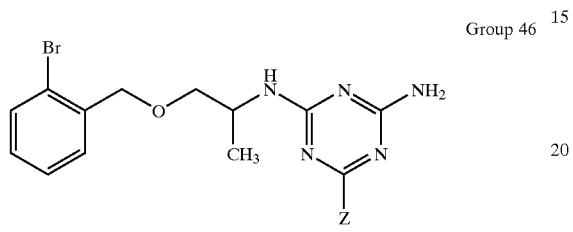

Here, Z has, for example, the meanings given above in group 1.

Group 47

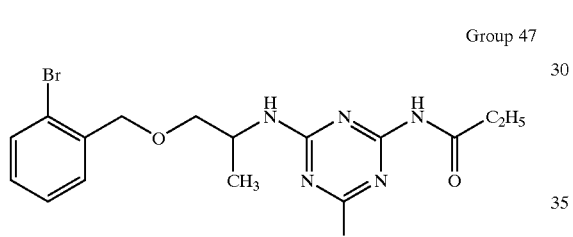

Here, Z has, for example, the meanings given above in group 1.

Group 48

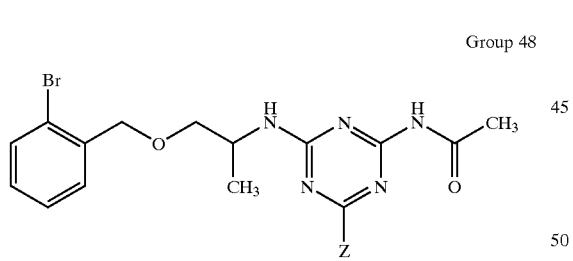

Here, Z has, for example, the meanings given above in group 1.

Group 49

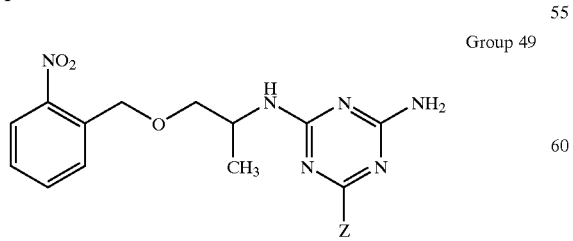

Here, Z has, for example, the meanings given above in group 1.

Group 50

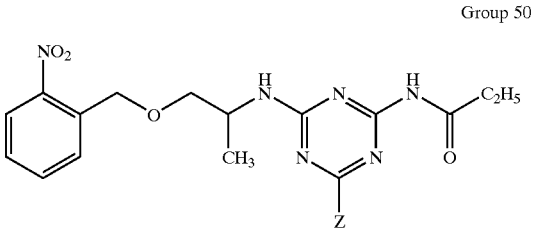

Here, Z has, for example, the meanings given above in group 1.

Group 51

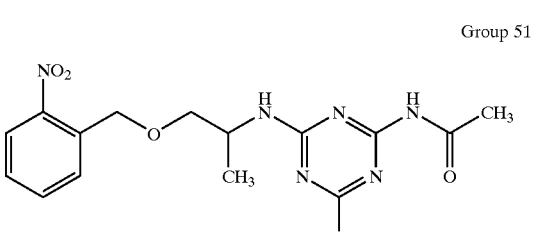

Here, Z has, for example, the meanings given above in group 1.

Group 52

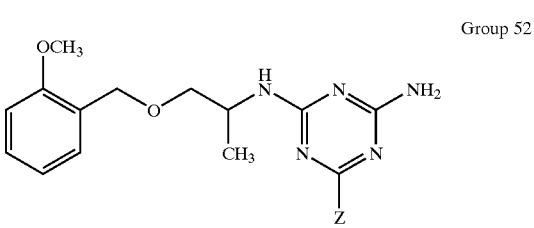

Here, Z has, for example, the meanings given above in group 1.

Group 53

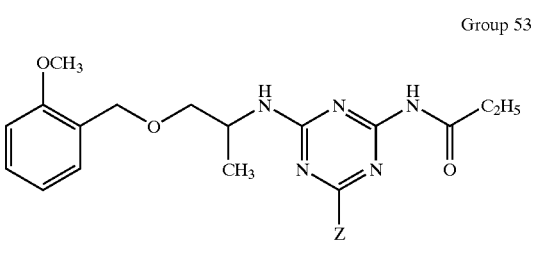

Here, Z has, for example, the meanings given above in group 1.

Group 54

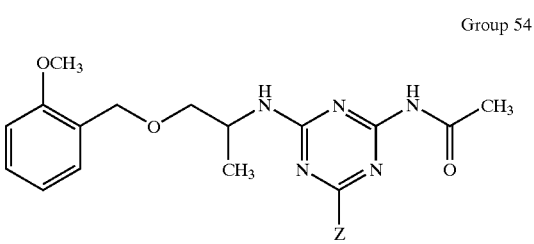

Here, Z has, for example, the meanings given above in group 1.

Group 55

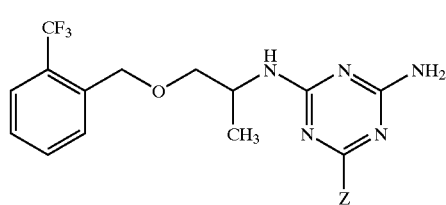

Here, Z has, for example, the meanings given above in group 1.

Group 56

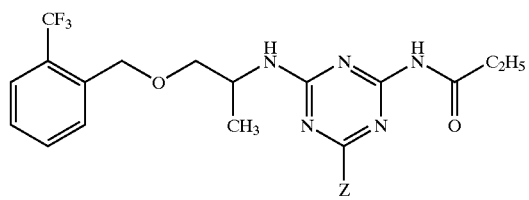

Here, Z has, for example, the meanings given above in group 1.

Group 57

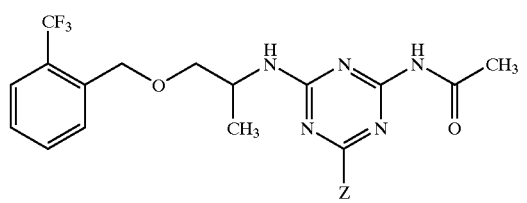

Here, Z has, for example, the meanings given above in group 1.

Group 58

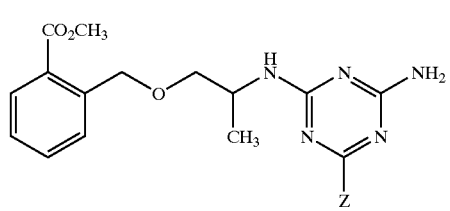

Here, Z has, for example, the meanings given above in group 1.

Group 59

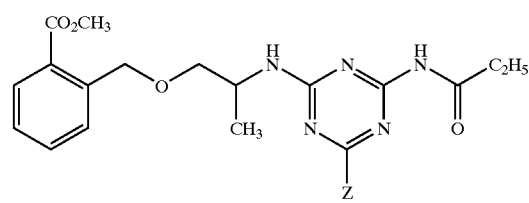

Here, Z has, for example, the meanings given above in group 1.

Group 60

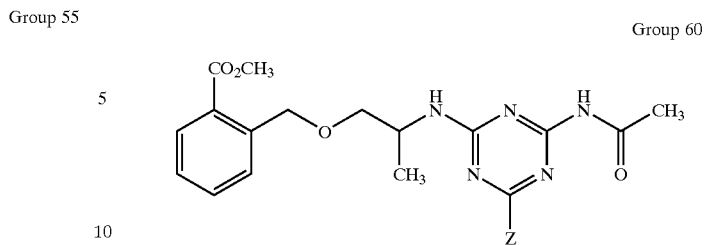

Here, Z has, for example, the meanings given above in group 1.

Group 61

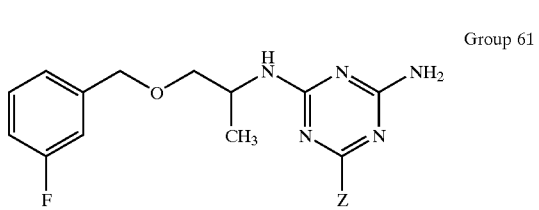

Here, Z has, for example, the meanings given above in group 1.

Group 62

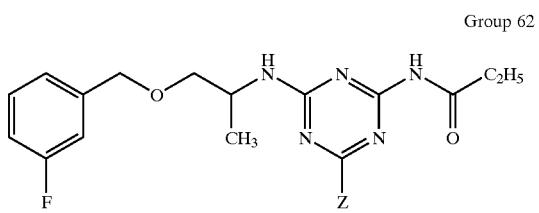

Here, Z has, for example, the meanings given above in group 1.

Group 63

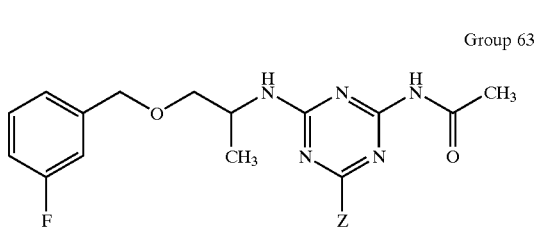

Here, Z has, for example, the meanings given above in group 1.

Group 64

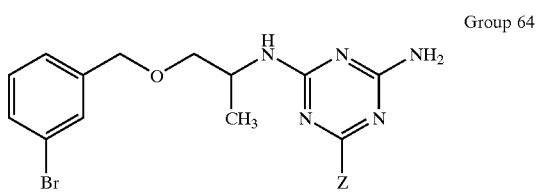

Here, Z has, for example, the meanings given above in group 1.

Group 65

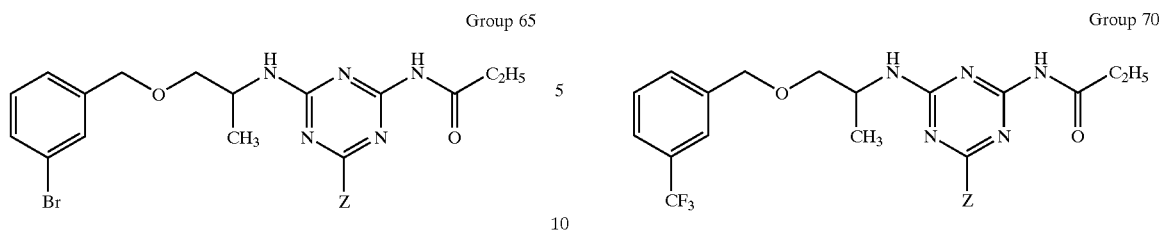

Here, Z has, for example, the meanings given above in group 1.

Group 66

Here, Z has, for example, the meanings given above in group 1.

Group 67

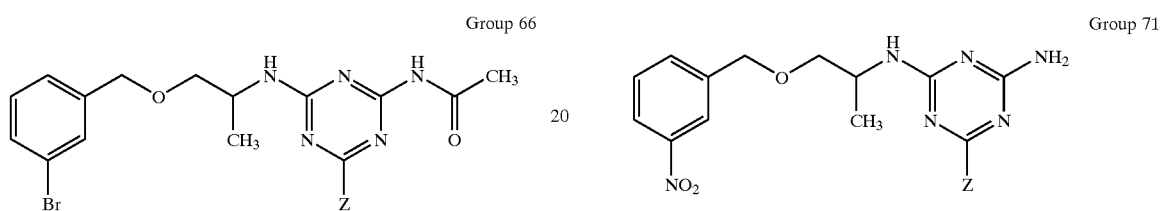

Here, Z has, for example, the meanings given above in group 1.

Group 68

Here, Z has, for example, the meanings given above in group 1.

Group 69

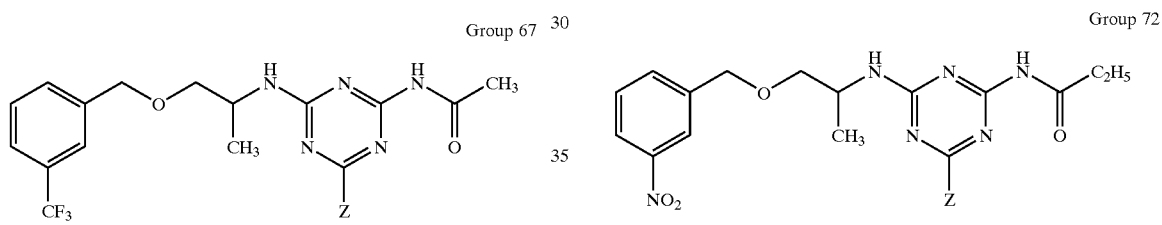

Here, Z has, for example, the meanings given above in group 1.

Group 70

Here, Z has, for example, the meanings given above in group 1.

Group 71

Here, Z has, for example, the meanings given above in group 1.

Group 72

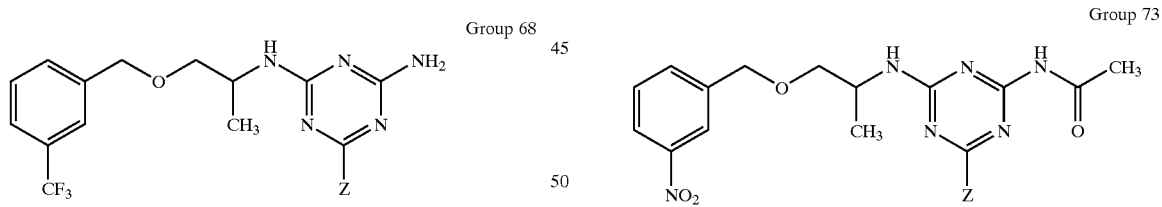

Here, Z has, for example, the meanings given above in group 1.

Group 73

Here, Z has, for example, the meanings given above in group 1.

Group 74

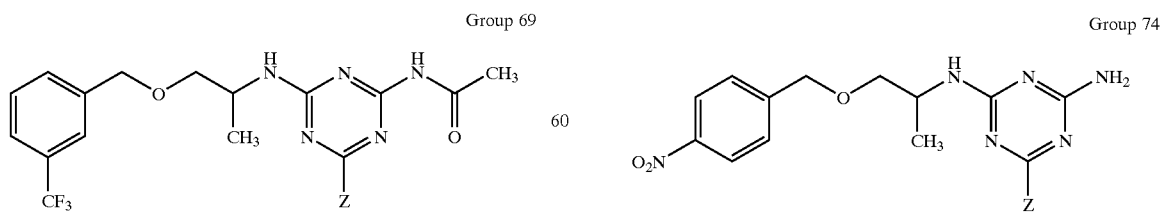

Here, Z has, for example, the meanings given above in group 1.

Group 75

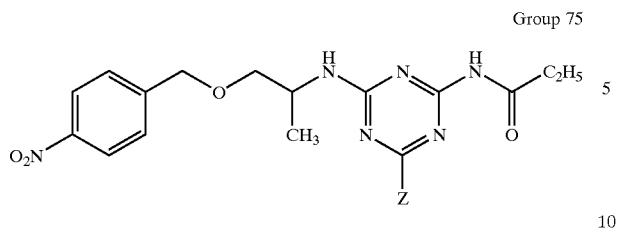

Here, Z has, for example, the meanings given above in group 1.

Group 76

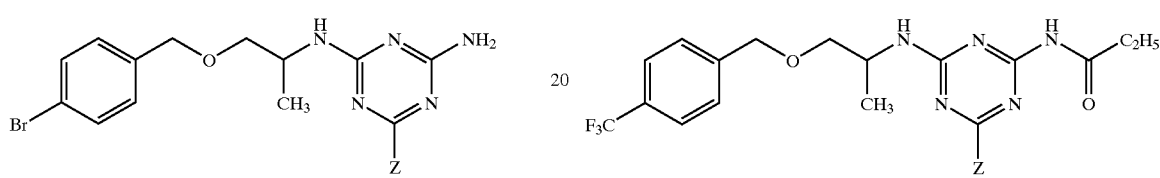

Here, Z has, for example, the meanings given above in group 1.

Group 77

Here, Z has, for example, the meanings given above in group 1.

Group 78

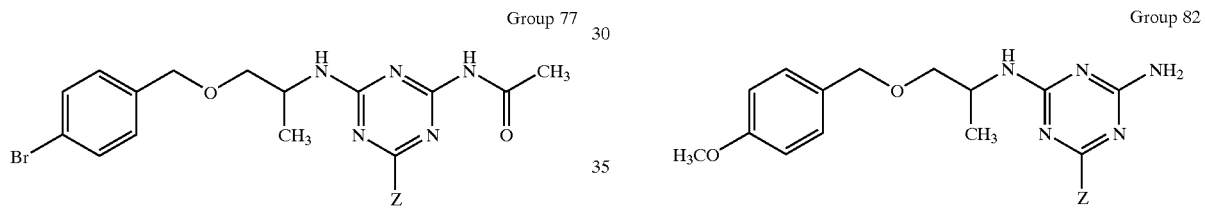

Here, Z has, for example, the meanings given above in group 1.

Group 79

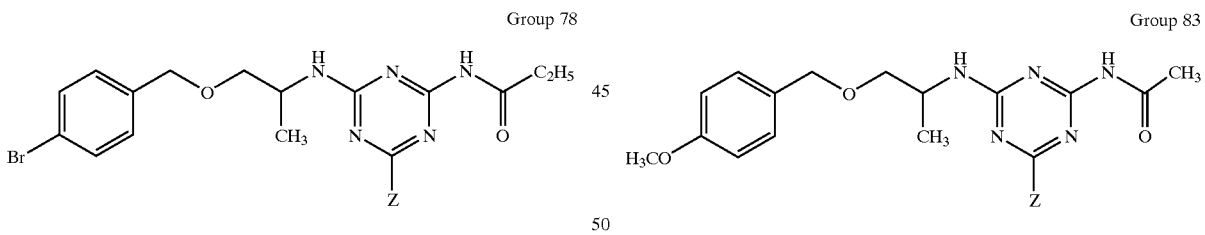

Here, Z has, for example, the meanings given above in group 1.

Group 80

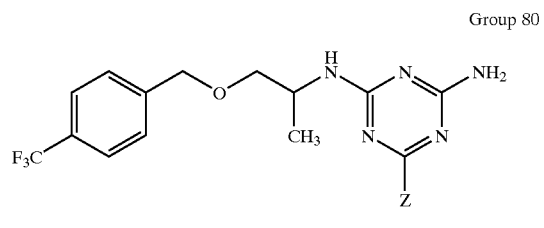

Here, Z has, for example, the meanings given above in group 1.

Group 81

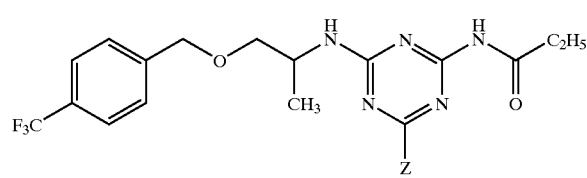

Here, Z has, for example, the meanings given above in group 1.

Group 82

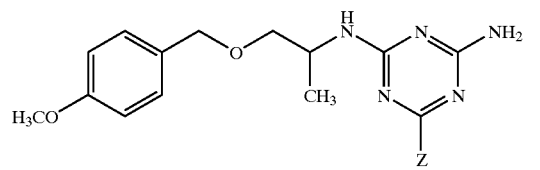

Here, Z has, for example, the meanings given above in group 1.

Group 83

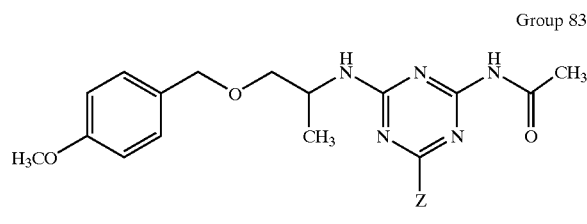

Here, Z has, for example, the meanings given above in group 1.

Group 84

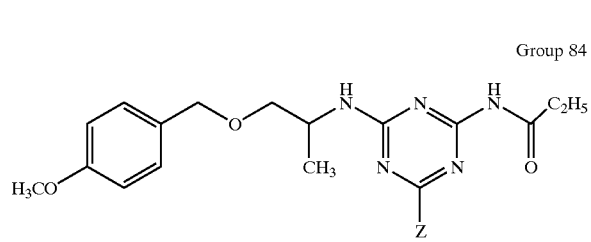

Here, Z has, for example, the meanings given above in group 1.

Group 85

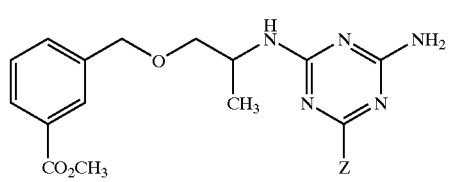

Here, Z has, for example, the meanings given above in group 1.

Group 86

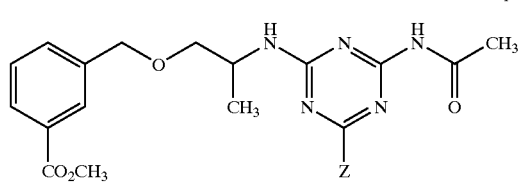

Here, Z has, for example, the meanings given above in group 1.

Group 87

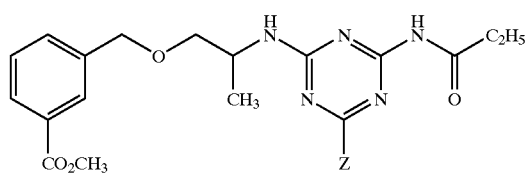

Here, Z has, for example, the meanings given above in group 1.

Group 88

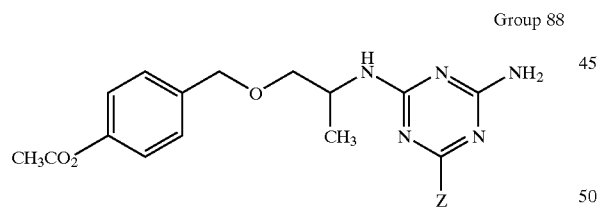

Here, Z has, for example, the meanings given above in group 1.

Group 89

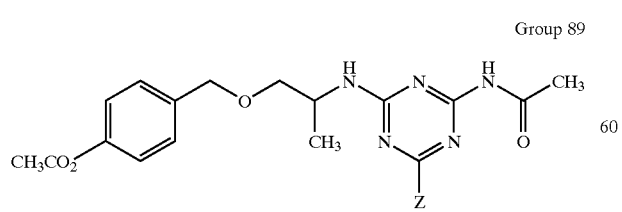

Here, Z has, for example, the meanings given above in group 1.

Group 90

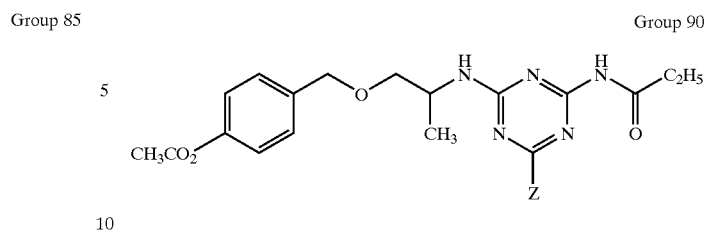

Here, Z has, for example, the meanings given above in group 1.

Group 91

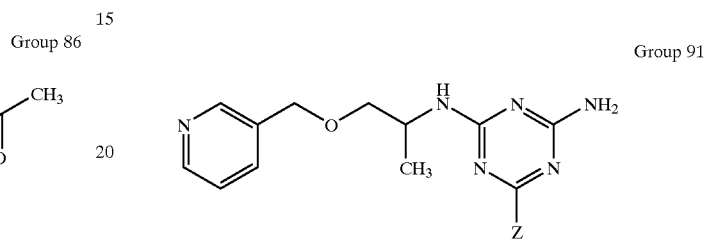

Here, Z has, for example, the meanings given above in group 1.

Group 92

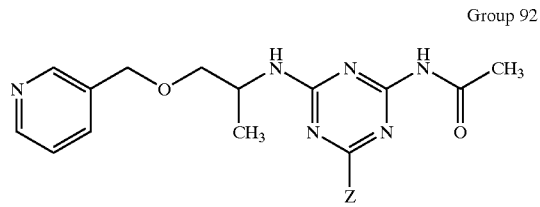

Here, Z has, for example, the meanings given above in group 1.

Group 93

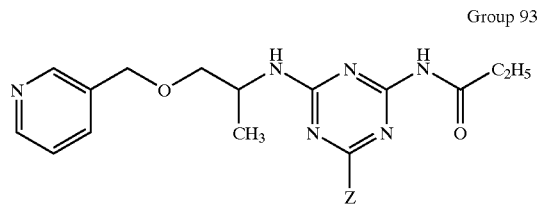

Here, Z has, for example, the meanings given above in group 1.

Group 94

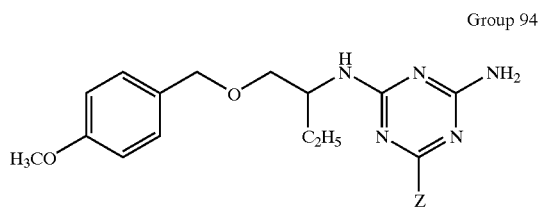

Here, Z has, for example, the meanings given above in group 1.

Group 95

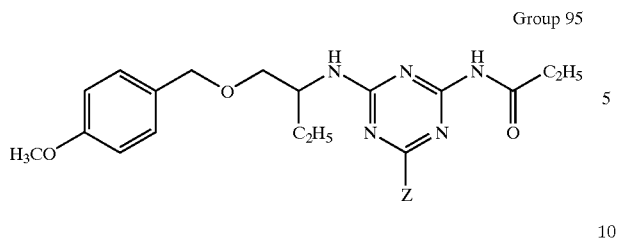

Here, Z has, for example, the meanings given above in group 1.

Group 96

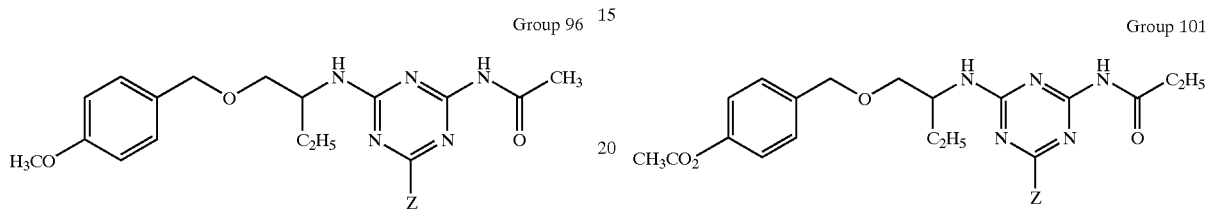

Here, Z has, for example, the meanings given above in group 1.

Group 97

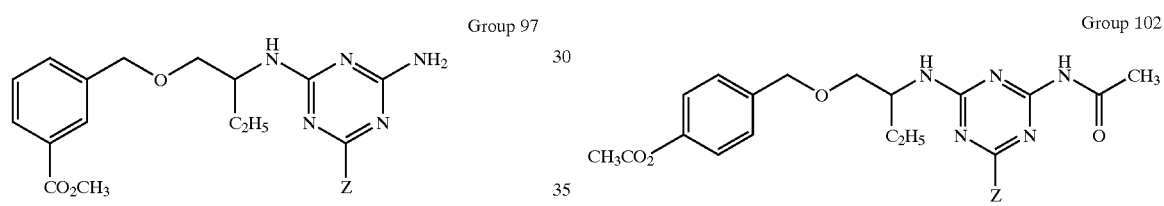

Here, Z has, for example, the meanings given above in group 1.

Group 98

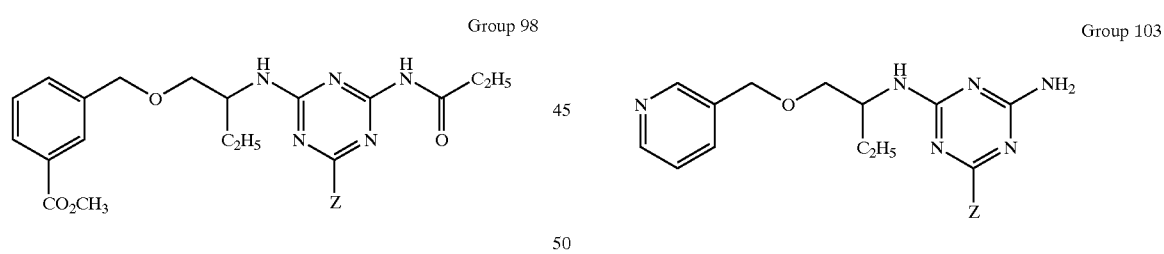

Here, Z has, for example, the meanings given above in group 1.

Group 99

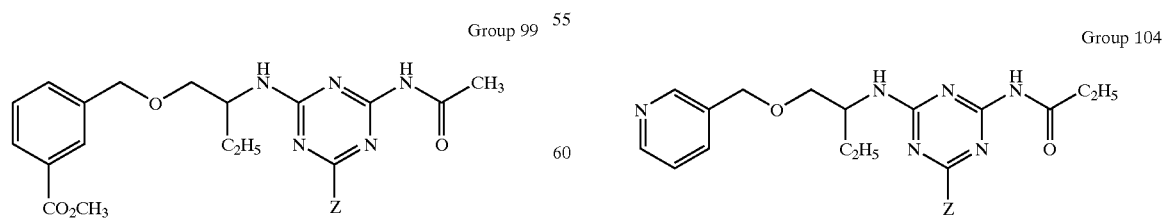

Here, Z has, for example, the meanings given above in group 1.

Group 100

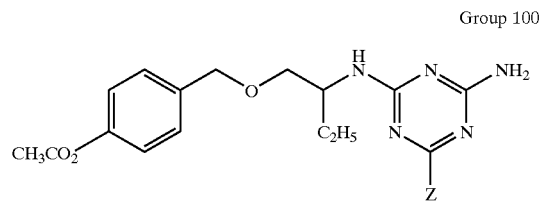

Here, Z has, for example, the meanings given above in group 1.

Group 101

Here, Z has, for example, the meanings given above in group 1.

Group 102

Here, Z has, for example, the meanings given above in group 1.

Group 103

Here, Z has, for example, the meanings given above in group 1.

Group 104

Here, Z has, for example, the meanings given above in group 1.

Group 105

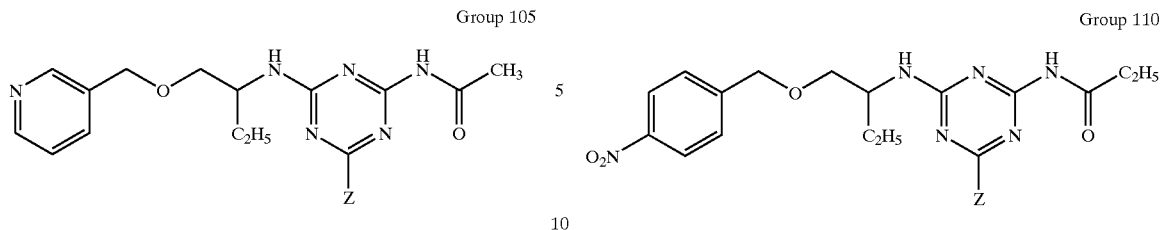

Here, Z has, for example, the meanings given above in group 1.

Group 106

Here, Z has, for example, the meanings given above in group 1.

Group 107

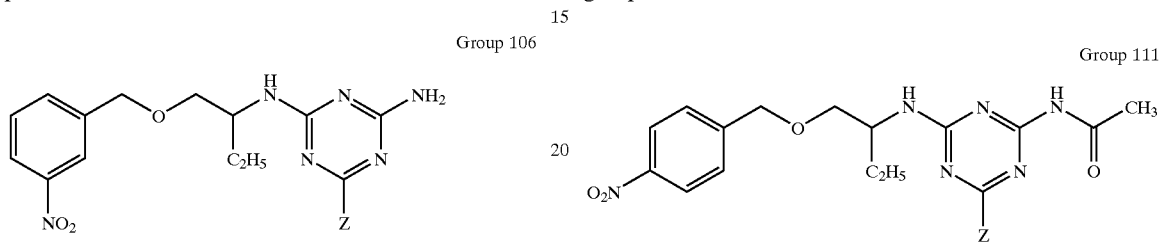

Here, Z has, for example, the meanings given above in group 1.

Group 108

Here, Z has, for example, the meanings given above in group 1.

Group 109

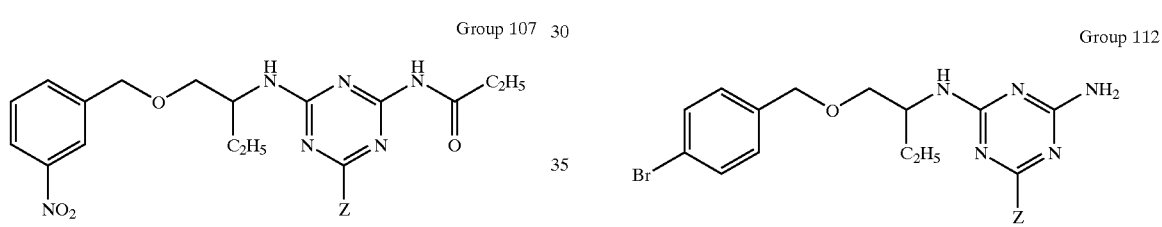

Here, Z has, for example, the meanings given above in group 1.

Group 110

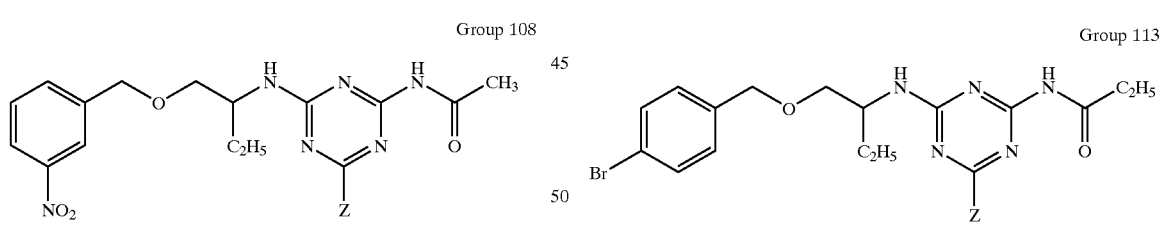

Here, Z has, for example, the meanings given above in group 1.

Group 111

Here, Z has, for example, the meanings given above in group 1.

Group 112

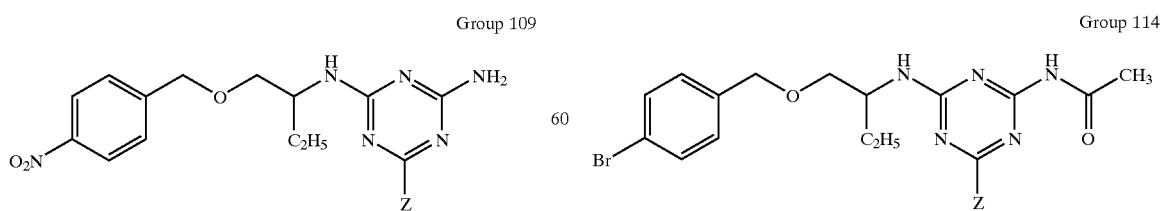

Here, Z has, for example, the meanings given above in group 1.

Group 113

Here, Z has, for example, the meanings given above in group 1.

Group 114

Here, Z has, for example, the meanings given above in group 1.

Group 115

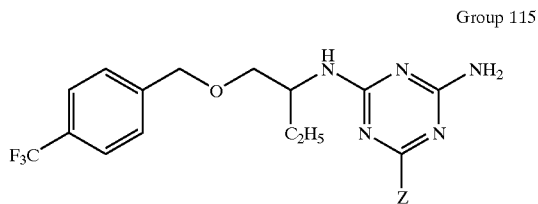

Here, Z has, for example, the meanings given above in group 1.

Group 116

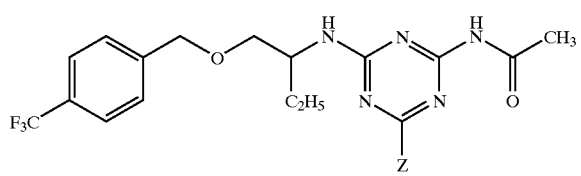

Here, Z has, for example, the meanings given above in group 1.

Group 117

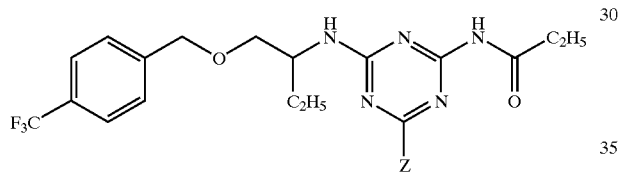

Here, Z has, for example, the meanings given above in group 1.

Group 118

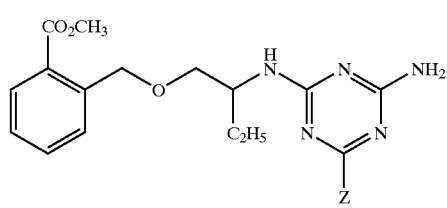

Here, Z has, for example, the meanings given above in group 1.

Group 119

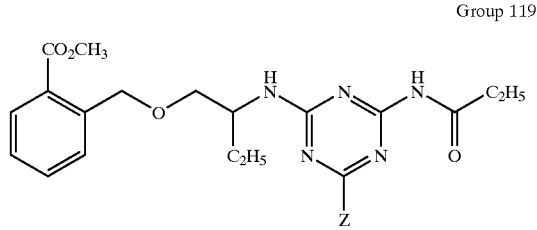

Here, Z has, for example, the meanings given above in group 1.

Group 120

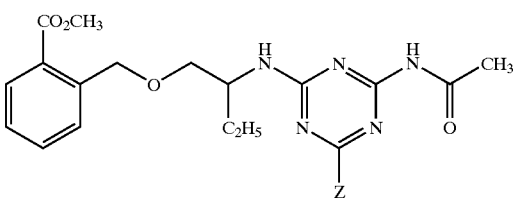

Here, Z has, for example, the meanings given above in group 1.

Group 121

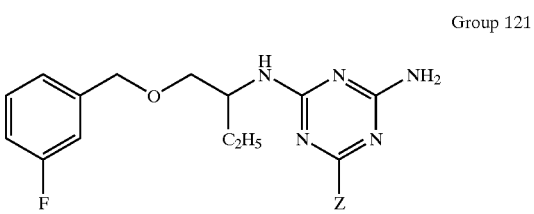

Here, Z has, for example, the meanings given above in group 1.

Group 122

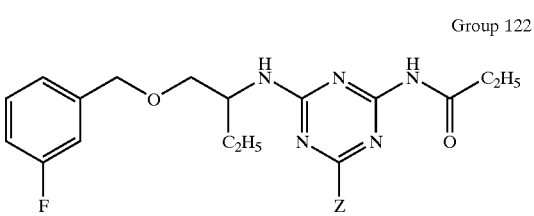

Here, Z has, for example, the meanings given above in group 1.

Group 123

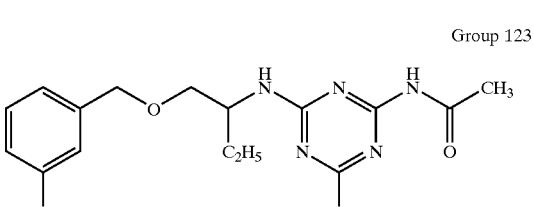

Here, Z has, for example, the meanings given above in group 1.

Group 124

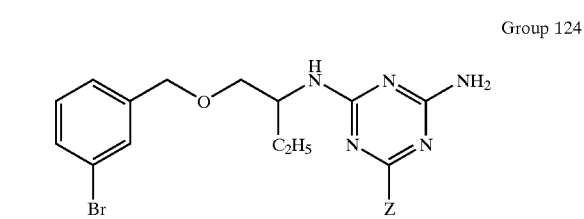

Here, Z has, for example, the meanings given above in group 1.

Group 125

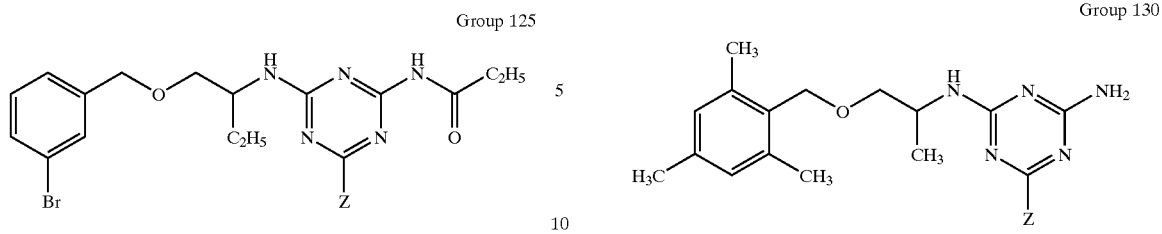

Here, Z has, for example, the meanings given above in group 1.

Group 126

Here, Z has, for example, the meanings given above in group 1.

Group 127

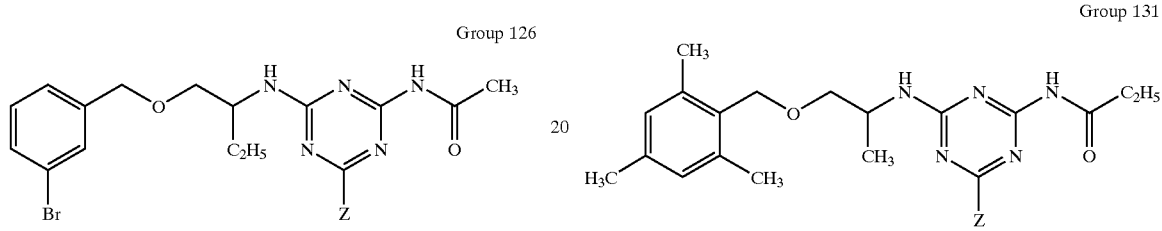

Here, Z has, for example, the meanings given above in group 1.

Group 128

Here, Z has, for example, the meanings given above in group 1.

Group 129

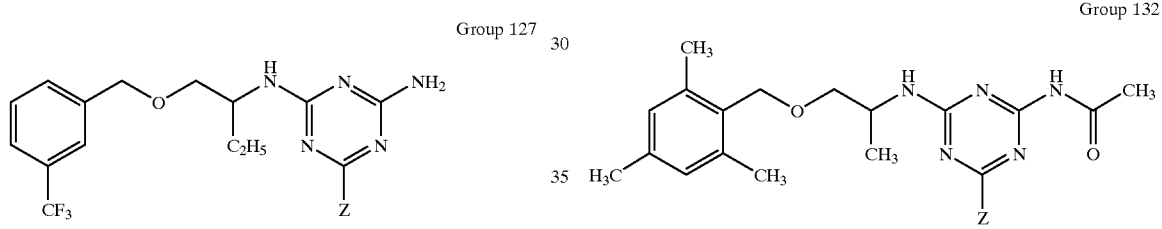

Here, Z has, for example, the meanings given above in group 1.

Group 130

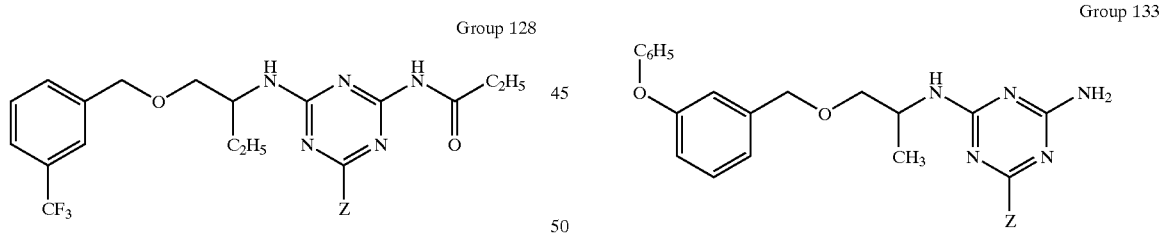

Here, Z has, for example, the meanings given above in group 1.

Group 131

Here, Z has, for example, the meanings given above in group 1.

Group 132

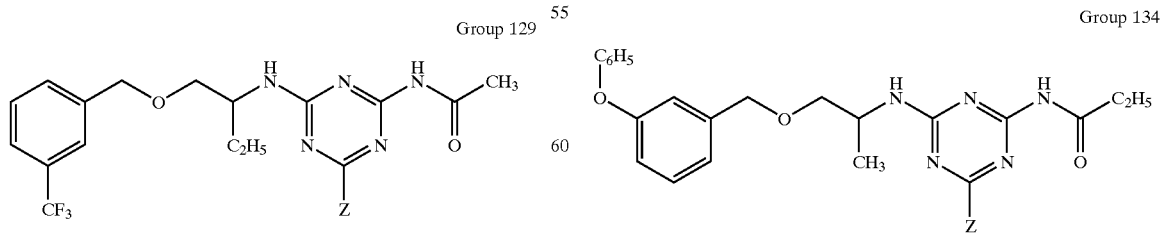

Here, Z has, for example, the meanings given above in group 1.

Group 133

Here, Z has, for example, the meanings given above in group 1.

Group 134

Here, Z has, for example, the meanings given above in group 1.

Group 135

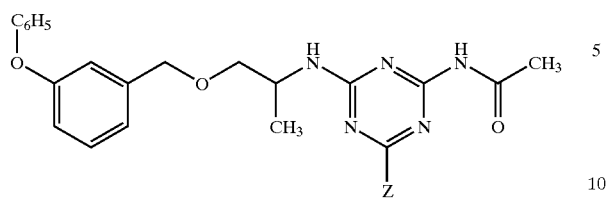

Here, Z has, for example, the meanings given above in group 1.

Group 136

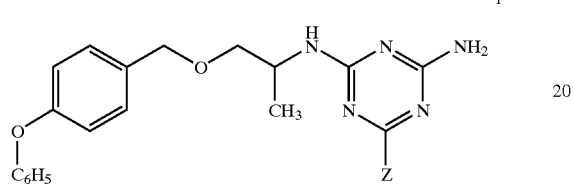

Here, Z has, for example, the meanings given above in group 1.

Group 137

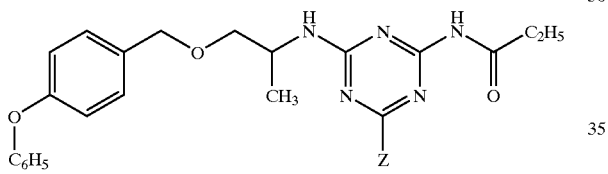

Here, Z has, for example, the meanings given above in group 1.

Group 138

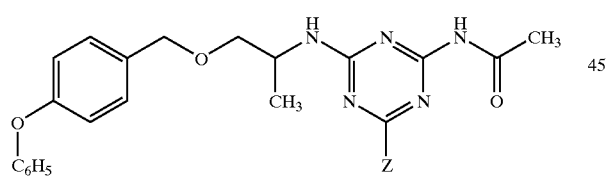

Here, Z has, for example, the meanings given above in group 1.

Group 139

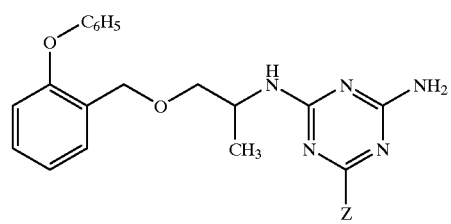

Here, Z has, for example, the meanings given above in group 1.

Group 140

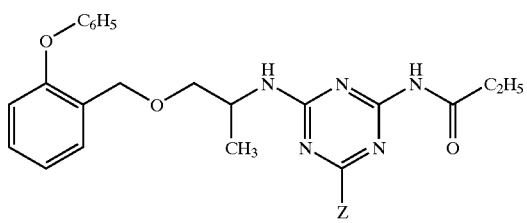

Here, Z has, for example, the meanings given above in group 1.

Group 141

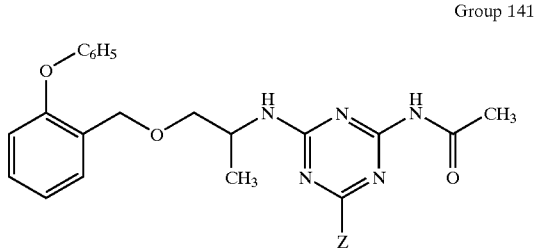

Here, Z has, for example, the meanings given above in group 1.

Group 142

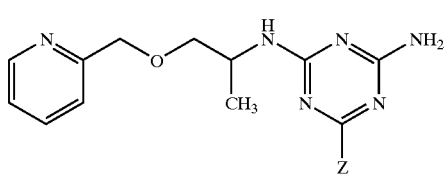

Here, Z has, for example, the meanings given above in group 1.

Group 143

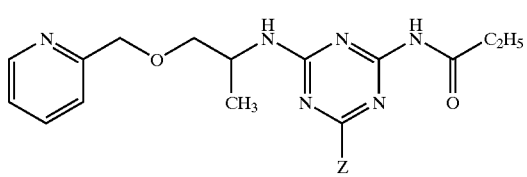

Here, Z has, for example, the meanings given above in group 1.

Group 144

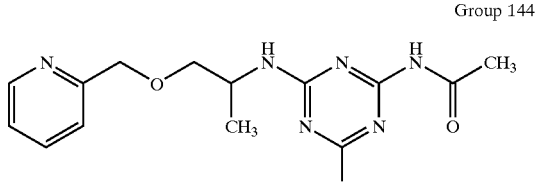

Here, Z has, for example, the meanings given above in group 1.

Group 145

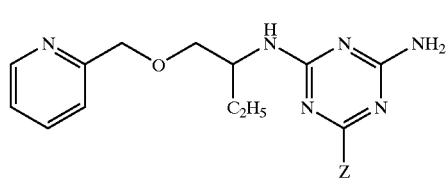

Here, Z has, for example, the meanings given above in group 1.

Group 146

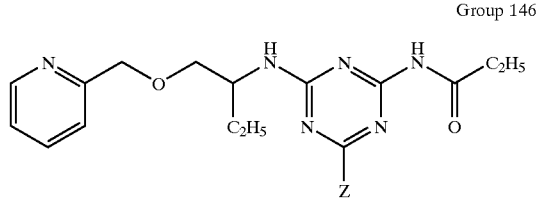

Here, Z has, for example, the meanings given above in group 1.

Group 147

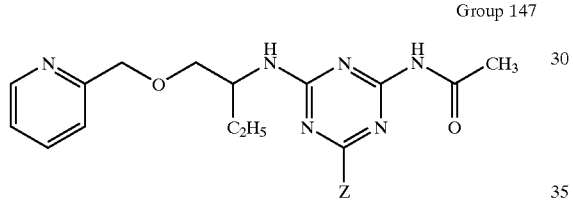

Here, Z has, for example, the meanings given above in group 1.

Group 148

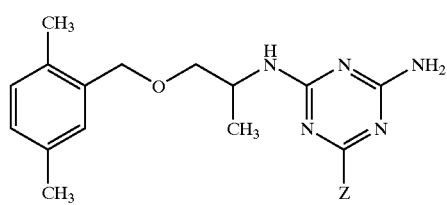

Here, Z has, for example, the meanings given above in group 1.

Group 149

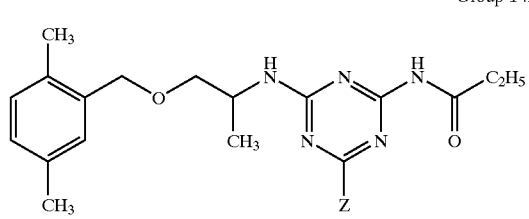

Here, Z has, for example, the meanings given above in group 1.

Group 150

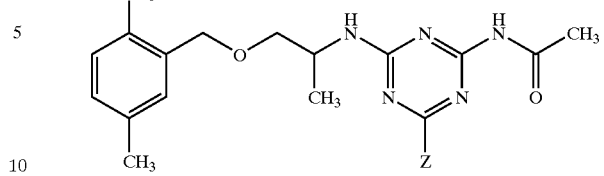

Here, Z has, for example, the meanings given above in group 1.

Using, for example, 1-(1-benzyloxymethyl-propyl)-biguanide and methyl trifluoroacetate as starting materials, the course of the reaction in the process (a) according to the invention can be illustrated by the following formula scheme:

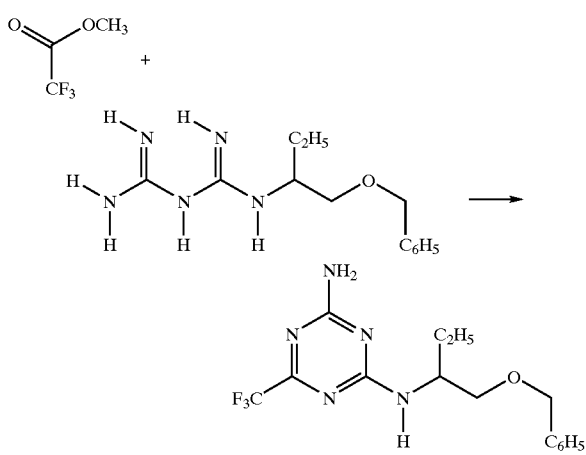

using, for example, 2-chloro-4-(1-benzylthiomethyl-propylamino)-6-trifluoromethyl. 1,3,5-triazine and ethylamine as starting materials, the course of the reaction in the process (b) according to the invention can be illustrated by the following formula scheme:

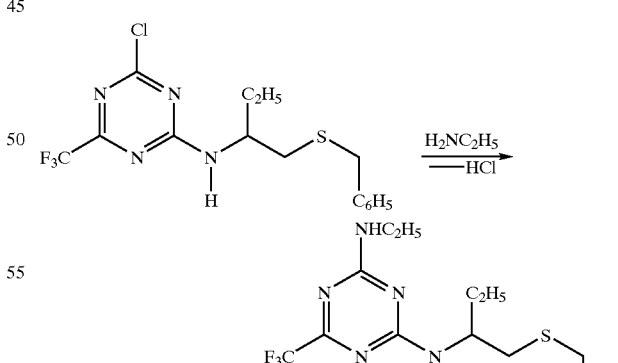

using, for example, 2-amino-4-methoxy-6-trifluoromethyl-1,3,5-triazine and 1-benzyloxymethyl-propylamine as starting materials, the course of the reaction in the process (c) according to the invention can be illustrated by the following formula scheme:

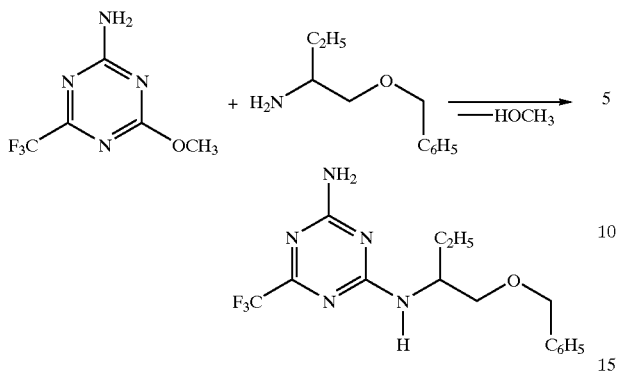

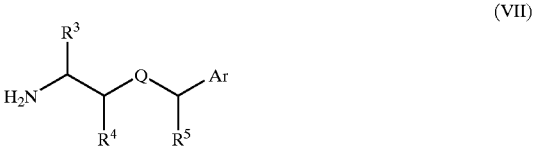

in which

Q, $R^3$, $R^4$, $R^5$ and Ar are as defined above and/or acid adducts of compounds of the general formula (VII), such as, for example, the hydrochlorides are reacted with cyanoguanidine ("dicyandiamide") of the formula (IX)

using, for example, 2-amino-4-(1-benzyloxymethyl-propylamino)-6-trifluoromethyl-1,3,5-triazine and acetyl chloride as starting materials, the course of the reaction in the process (d) according to the invention can be illustrated by the following formula scheme:

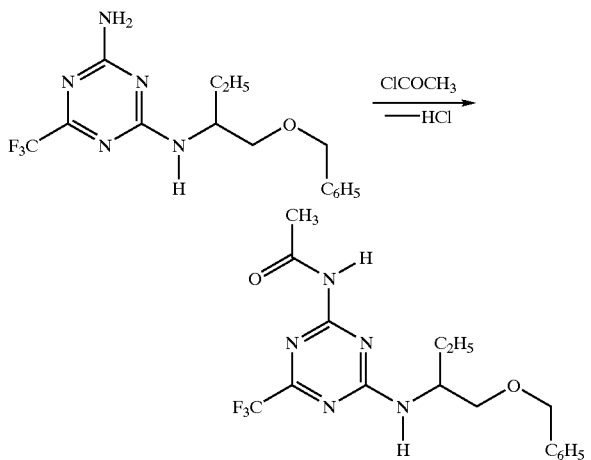

if appropriate in the presence of a reaction auxiliary, such as, for example, hydrogen chloride, and if appropriate in the presence of a diluent, such as, for example, n-decane or 1,2-dichloro-benzene, at temperatures between 100° C. and 200° C. (cf EP-492 615, Preparation Examples).

The substituted alkylamines of the general formula (VII) required as precursors for this purpose are known and/or can be prepared by processes known per se (cf. J. Org. Chem. 34 (1969), 466–468; J. Heterocycl. Chem. 11 (1974), 985–989; Liebigs Ann. Chem. 1980, 786–790; Can. J. Chem. 60 (1982), 1836–1841; Tetrahedron 40 (1984), 1255–1268; J. Am. Chem. Soc. 109 (1987), 236–239 and 1798–1805; loc. cit. 110 1988), 3862–3869; Tetrahedron Lett. 30 (1989), 731–734; Tetrahedron: Asymmetry 3 (1992), 587–590; loc. cit. 7 (1996), 3397–3406; Tetrahedron Lett. 34 (1993), 2957–2960; Tetrahedron 51 (1995), 1709–1720; J. Org. Chem. 61 (1996), 7285–7290; Tetrahedron 52 (1996), 4199–4214; EP-192 060; EP-199 845; WO 9213823; Preparation Examples).

The formula (II) provides a general definition of the biguanides to be used as starting materials in the process (a) according to the invention for preparing compounds of the formula (I). In the formula (II), Q, $R^1$, $R^2$, $R^3$, $R^4$, $R^5$ and Ar preferably or in particular have those meanings which have already been mentioned above, in connection with the description of the compounds of the formula (I) according to the invention, as being preferred or as being particularly preferred for Q, $R^1$, $R^2$, $R^3$, $R^4$, $R^5$ and Ar.

Suitable acid adducts of compounds of the formula (II) are their addition products with protic acids, such as, for example, with hydrogen chloride, hydrogen bromide, sulphuric acid, methanesulphonic acid, benzenesulphonic acid and p-toluenesulphonic acid.

The starting mate rials of the general formula (II) have hitherto not been disclosed in the literature; as novel substances, they also form part of the subject-matter of the present application.

The novel biguanides of the general formula (II) are obtained when substituted alkylamines of the general formula (VII)

The formula (III) provides a general definition of the alkoxycarbonyl compounds further to be used as starting materials in the process (a) according to the invention for preparing compounds of the formula (I). In the formula (III), Z preferably or in particular has that meaning which has already been mentioned above, in connection with the description of the compounds of the formula (I) according to the invention, as being preferred or as being particularly preferred for Z; R' preferably represents alkyl having 1 to 4 carbon atoms, in particular methyl or ethyl.

The starting materials of the formula (III) are known chemicals for synthesis.

The formula (IV) provides a general definition of the substituted halogenotriazines to be used as starting materials in the process (b) according to the invention for preparing compounds of the formula (I). In the formula (IV), Q, $R^3$, $R^4$, $R^5$, Ar and Z preferably or in particular have those meanings which have already been mentioned above, in connection with the description of the compounds of the formula (I) according to the invention, as being preferred or as being particularly preferred for Q, $R^3$, $R^4$, $R^5$, Ar and Z; X preferably represents fluorine or chlorine, in particular chlorine.

The starting materials of the general formula (IV) have hitherto not been disclosed in the literature; as novel substances, they also form part of the subject-matter of the present application.

The novel substituted halogenotriazines of the general formula (IV) are obtained when corresponding dihalogenotriazines of the general formula (X)

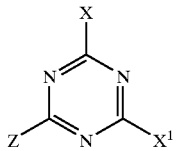

(X)

in which
X and Z are as defined above and
$X^1$ represents halogen
are reacted with substituted alkylamines of the general formula (VII)

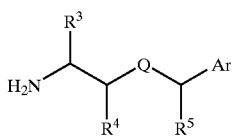

(VII)

in which
Q, $R^3$, $R^4$, $R^5$ and Ar are as defined above,
if appropriate in the presence of an acid acceptor, such as, for example, ethyldiisopropylamine, and if appropriate in the presence of a diluent, such as, for example, tetrahydrofuran or dioxane, at temperatures between −50° C. and +50° C. (cf. the Preparation Examples).

The formula (V) provides a general definition of the nitrogen compounds further to be used as starting materials in the process (b) according to the invention for preparing compounds of the formula (I). In the formula (V), $R^1$ and $R^2$ preferably or in particular have those meanings which have already been mentioned above, in connection with the description of the compounds of the formula (I) according to the invention, as being preferred or as being particularly preferred for $R^1$ and $R^2$.

The starting materials of the general formula (V) are known chemicals for synthesis. The formula (VI) provides a general definition of the substituted aminotrazines to be used as starting materials in the process (c) according to the invention for preparing compounds of the formula (I). In the formula (VI) $R^1$, $R^2$ and Z preferably or in particular have those meanings which have already been mentioned above, in connection with the description of the compounds of the formula (I) according to the invention, as being preferred or as being particularly preferred for $R^1$, $R^2$ and Z; $Y^1$ preferably represents fluorine, chlorine, methoxy or ethoxy, in particular chlorine or methoxy.

The starting materials of the general formula (VI) are known and/or can be prepared by processes known per se (cf. WO 95/11237).

The formula (VII) provides a general definition of the substituted alkylamines further to be used as starting materials in the process (c) according to the invention. In the formula (VII), Q, $R^3$, $R^4$, $R^5$ and Ar preferably or in particular have those meanings which have already been mentioned above, in connection with the description of the compounds of the formula (I) according to the invention, as being preferred or as being particularly preferred for Q, $R^3$, $R^4$, $R^5$ and Ar.

The starting materials of the general formula (VII) are known and/or can be prepared by processes known per se (cf. J. Org. Chem. 34 (1969), 466–468; J. Heterocycl. Chem. 11 (1974), 985–989; Liebigs Ann. Chem. 1980, 786–790; Can. J. Chem. 60 (1982), 1836–1841; Tetrahedron 40 (1984), 1255–1268; J. Am. Chem. Soc. 109 (1987), 236–239; loc. cit. 110 (1988), 3862–3869; Tetrahedron Lett. 30 (1989), 731–734; Tetrahedron: Asymmetry 3 (1992), 587–590; Tetrahedron Lett. 34 (1993), 2957–2960; EP-192 060; EP-199 845; WO 9213823; Preparation Examples).

The formula (Ia) provides a general definition of the substituted 2,4-diamino-1,3,5-triazines to be used as starting materials in the process (d) according to the invention for preparing compounds of the formula (I). In the formula (Ia), Q, $R^1$, $R^3$, $R^4$, $R^5$, Ar and Z preferably or in particular have those meanings which have already been mentioned above, in connection with the description of the compounds of the formula (I) according to the invention, as being preferred or as being particularly preferred for Q, $R^1$, $R^3$, $R^4$, $R^5$, Ar and Z.

As novel substances, the starting materials of the general formula (Ia) also form part of the subject-matter of the present application; they can be prepared by the processes (a), (b) or (c) according to the invention (cf. the Preparation Examples).

The formula (VIII) provides a general definition of the alkylating or acylating agents further to be used as starting materials in the process (d) according to the invention. In the formula (VIII), $R^2$ has, with the exception of hydrogen, preferably or in particular that meaning which has already been mentioned above, in connection with the description of the compounds of the formula (I) according to the invention, as being preferred or as being particularly preferred for $R^2$; $Y^2$ preferably represents fluorine, chlorine, bromine, methoxy, ethoxy, acetyloxy or propionyloxy, in particular chlorine, methoxy or acetyloxy.

The starting materials of the general formula (VIII) are known chemicals for synthesis.

The processes of the invention for preparing the compounds of the formula (I) are, if appropriate, carried out using a reaction auxiliary. Suitable reaction auxiliaries for the processes (a), (b), (c) and (d) are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diusopropylamine, N,N-dimethylcyclohexylamine, dicyclohexylamine, ethyl-dicyclohexylamine, N,N-dimethylaniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methylpyridine, 4-dimethylamino-pyridine, N-methyl-piperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

Suitable for use as reaction auxiliaries are, if appropriate, also molecular sieves.

Suitable diluents for carrying out the processes (a), (b), (c) and (d) according to the invention are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as methyl isopropyl ketone or methyl isobutyl ketone; nitriles, such as acetonitrile, propionitrile or butyronitrile; amides, such as N,N-dimethylformamide, N,N-dimethylacetamide, N-methyl-formanilide, N-methylpyrrolidone or hexamethylphosphoric triamide; esters, such as methyl acetate or ethyl acetate, sulphoxides, such as dimethyl sulphoxide; alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water or pure water.

When carrying out the processes (a), (b), (c) and (d) according to the invention, the reaction temperatures can be varied within a relatively wide range. In general, the processes are carried out at temperatures between −20° C. and +300° C., preferably between −10° C. and +250° C.

The processes (a), (b), (c) and (d) according to the invention are generally carried out under atmospheric pressure. However, it is also possible to carry out the processes according to the invention under elevated or reduced pressure - in general between 0.1 bar and 10 bar.

For carrying out the processes according to the invention, the starting materials are generally employed in approximately equimolar amounts. However, it is also possible to employ in each case one of the components in a relatively large excess. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:
Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.
Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis, Cucurbita.
Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus, Apera.
Monocotyledonous crops of the genera: Oryza, Zea, Triticum, Hordeum, Avena, Secale, Sorghum, Panicum, Saccharum, Ananas, Asparagus, Allium.

However, the use of the active compounds according to the invention is in no way restricted to these genera, but also extends in the same manner to other plants.

Depending on the concentration, the compounds are suitable for total weed control, for example on industrial terrain and rail tracks and on paths and areas with or without tree growth. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention are particularly suitable for selective control of monocotyledonous and dicotyledonous weeds in monocotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephakins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlornitrofen, chlorsulfuron, chlorotoluron, cinmethylin, cinosulfuron, clethodim, clodinafop(-propargyl), clomazone, clomeprop, clopyralid, clopyrasulfuron(-methyl), cloransulam(-methyl), cumyluron, cyanazine, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, ethametsulfuron(-methyl), ethofumesate, ethoxyfen, ethoxysulfuron, etobenzanid, fenoxaprop-(-P-ethyl), flamprop(-isopropyl), flamprop(-isopropyl-L), flamprop(-methyl), flazasulfuron, fluazifop(-P-butyl), flumetsulam, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthliacet(-methyl), fluthiamide, fomesafen, glufosinate(-ammonium), glyphosate(-isopropylammonium), halosafen, haloxyfop(-ethoxyethyl), haloxyfop(-p-methyl), hexazinone, imazamethabenz-(-methyl), imazamethapyr, imazamox, imazapyr, imazaquin, imazethapyr, imazosulfuron, ioxynil, isopropalin, isoproturon, isouron, isoxaben, isoxaflutole, isoxapyrifop, lactofen, lenacil, linuron, MCPA, MCPP, mefenacet, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazasulfuron(-ethyl), pyrazoxyfen, pyribenzoxim, pyributicarb, pyridate, pyriminobac-(-methyl), pyrithiobac(-sodium), quinchlorac, quinmerac, quinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES:

Example 1

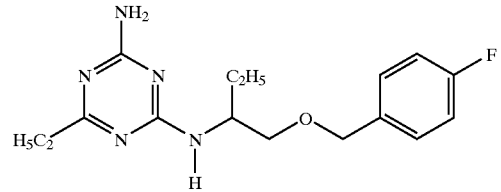

(Process (a))

At −10° C., a solution of 1.08 g (20 mmol) of sodium methoxide in 5 ml of methanol is added dropwise with stirring to a mixture of 3.18 g (10 mmol) of 1-[1-(4-fluorobenzyloxymethyl)-propyl]-biguanide hydrochloride (racemic) and 2.8 g of powdered molecular sieve (4 Å) in 10 ml of methanol. 1.14 ml (10 mmol) of ethyl propionate are then added dropwise. The reaction mixture is allowed to warm to room temperature (about 20° C.) and stirred for another 15 hours. Solids and molecular sieve are then filtered off with suction from the precipitated mixture, the filtrate is concentrated and the residue is taken up in ethyl acetate. After washing with water, drying over sodium sulphate and concentration under water pump vacuum, the residue is worked up by column chromatography (silica gel, ethyl acetate/petroleum ether).

This gives 1.4 g (44% of theory) of 2-amino-4-ethyl-6-[1-(4-fluorobenzyloxymethyl)-propylamino]-1,3,5-triazine (racemate) of melting point 96° C.

Example 2

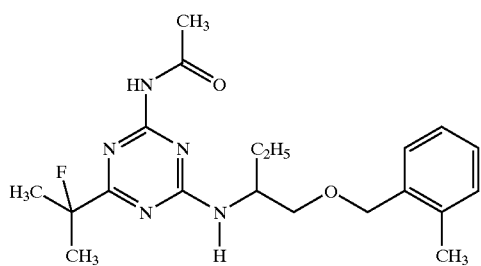

(Process (d))

2-Amino-4-(1-fluoro-1-methyl-ethyl)-6-[1-(2-methyl-benzyloxymethyl-1-propylamino]-1,3,5-triazine (racemic, 260 mg, 0.75 mmol) in acetic anhydride (5 ml) is heated at 100° C. for 1 hour. After cooling to room temperature, the mixture is admixed with water (10 ml), and stirred for one hour, and the precipitated product is isolated by filtration with suction.

This gives 140 mg (50% of theory) of 2-acetylamino-4-(1-fluoro-1-methyl-ethyl-6-[1-(2-methyl-benzyloxymethyl)-propylamino]-1,3,5-triazine (racemate) of melting point 108° C.

Analogously to Examples 1 and 2, and in accordance with the general description of the Preparation Processes according to the invention, it is also possible to prepare, for example, the compounds of the formula (I) listed in Table 1 below.

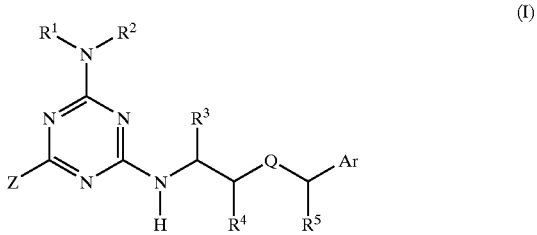
(I)

TABLE 1

Examples of compounds of the formula (I)

| Ex. No. | $R^1$ | $R^2$ | $R^3$ | $R^4$ | $R^5$ | Ar | Q | Z | Physical data and stereochem. specifications |
|---|---|---|---|---|---|---|---|---|---|
| 3 | H | H | $CH_3$ | H | H | phenyl | O | $CH_2CH_3$ | m.p.: 104° C. (racemate) |
| 4 | H | H | $CH_3$ | H | H | phenyl | O | $CHFCH_3$ | m.p.: 105° C. (racemate) |
| 5 | H | H | $CH_3$ | H | H | phenyl | O | $C(CH_3)_2F$ | m.p.: 114° C. (racemate) |
| 6 | H | H | $C_2H_5$ | H | H | phenyl | O | $CH_2CH_3$ | m.p.: 95° C. (racemate) |
| 7 | H | H | $C_2H_5$ | H | H | phenyl | O | $CHFCH_3$ | m.p.: 98° C. (racemate) |
| 8 | H | H | $C_2H_5$ | H | H | phenyl | O | $C(CH_3)_2F$ | m.p.: 114° C. (racemate) |
| 9 | H | H | $C_2H_5$ | H | H | 2-Cl-phenyl | O | $CH_2CH_3$ | m.p.: 118° C. (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 10 | H | H | $C_2H_5$ | H | H | 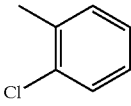 2-Cl-C₆H₄ | O | CHFCH₃ | m.p.: 126° C. (racemate) |
| 11 | H | H | $C_2H_5$ | H | H | 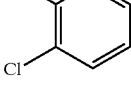 2-Cl-C₆H₄ | O | C(CH₃)₂F | m.p.: 115° C. (racemate) |
| 12 | H | H | $C_2H_5$ | H | H | 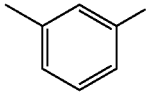 3-Cl-C₆H₄ | O | CH₂CH₃ | m.p.: 89° C. (racemate) |
| 13 | H | H | $C_2H_5$ | H | H | 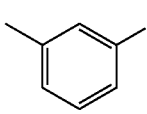 3-Cl-C₆H₄ | O | CHFCH₃ | m.p.: 104° C. (racemate) |
| 14 | H | H | $C_2H_5$ | H | H | 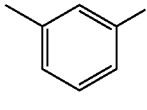 3-Cl-C₆H₄ | O | C(CH₃)₂F | m.p.: 104° C. (racemate) |
| 15 | H | H | $C_2H_5$ | H | H | 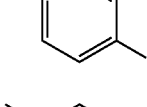 4-Cl-C₆H₄ | O | CH₂CH₃ | m.p.: 105° C. (racemate) |
| 16 | H | H | $C_2H_5$ | H | H | 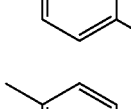 4-Cl-C₆H₄ | O | CHFCH₃ | m.p.: 100° C. (racemate) |
| 17 | H | H | $C_2H_5$ | H | H | 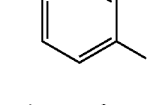 4-Cl-C₆H₄ | O | C(CH₃)₂F | m.p.: 102° C. (racemate) |
| 18 | H | H | $C_2H_5$ | H | H | 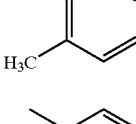 2-CH₃-C₆H₄ | O | CH₂CH₃ | m.p.: 102° C. (racemate) |
| 19 | H | H | $C_2H_5$ | H | H | 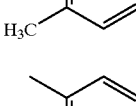 2-CH₃-C₆H₄ | O | CHFCH₃ | m.p.: 104° C. (racemate) |
| 20 | H | H | $C_2H_5$ | H | H | 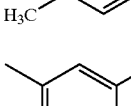 2-CH₃-C₆H₄ | O | C(CH₃)₂F | m.p.: 106° C. (racemate) |
| 21 | H | H | $C_2H_5$ | H | H | 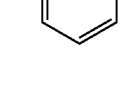 3-CH₃-C₆H₄ | O | CH₂CH₃ | m.p.: 99° C. (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 22 | H | H | C₂H₅ | H | H | 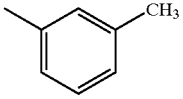 3-CH₃-C₆H₄ | O | CHFCH₃ | m.p.: 102° C. (racemate) |
| 23 | H | H | C₂H₅ | H | H | 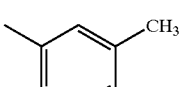 3-CH₃-C₆H₄ | O | C(CH₃)₂F | m.p.: 107° C. (racemate) |
| 24 | H | H | C₂H₅ | H | H | 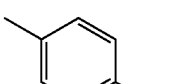 4-CH₃-C₆H₄ | O | CH₂CH₃ | m.p.: 94° C. (racemate) |
| 25 | H | H | C₂H₅ | H | H | 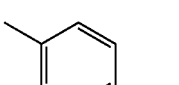 4-CH₃-C₆H₄ | O | CHFCH₃ | m.p.: 96° C. (racemate) |
| 26 | H | H | C₂H₅ | H | H | 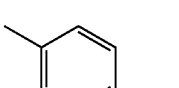 4-CH₃-C₆H₄ | O | C(CH₃)₂F | m.p.: 116° C. (racemate) |
| 27 | H | H | C₂H₅ | H | H | 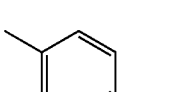 2,4-Cl₂-C₆H₃ | O | CH₂CH₃ | m.p.: 113° C. (racemate) |
| 28 | H | H | C₂H₅ | H | H | 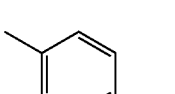 2,4-Cl₂-C₆H₃ | O | CHFCH₃ | m.p.: 103° C. (racemate) |
| 29 | H | H | C₂H₅ | H | H | 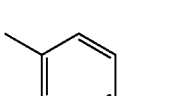 2,4-Cl₂-C₆H₃ | O | C(CH₃)₂F | m.p.: 112° C. (racemate) |
| 30 | H | H | C₂H₅ | H | H | 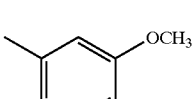 3-OCH₃-C₆H₄ | O | CH₂CH₃ | m.p.: 92° C. (racemate) |
| 31 | H | H | C₂H₅ | H | H | 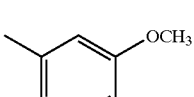 3-OCH₃-C₆H₄ | O | CHFCH₃ | m.p.: 95° C. (racemate) |
| 32 | H | H | C₂H₅ | H | H | 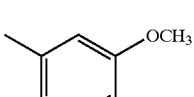 3-OCH₃-C₆H₄ | O | C(CH₃)₂F | m.p.: 98° (racemate) |
| 33 | H | H | C₂H₅ | H | H | 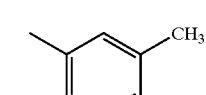 2,5-(CH₃)₂-C₆H₃ | O | CH₂CH₃ | m.p.: 129° C. (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 34 | H | H | $C_2H_5$ | H | H | 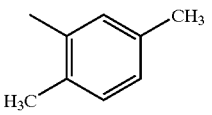 | O | $CHFCH_3$ | m.p.: 134° C. (racemate) |
| 35 | H | H | $C_2H_5$ | H | H | 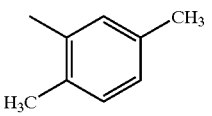 | O | $C(CH_3)_2F$ | m.p.: 143° C. (racemate) |
| 36 | H | H | $C_2H_5$ | H | H | 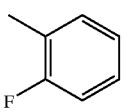 | O | $CH_2CH_3$ | m.p.: 92° C. (racemate) |
| 37 | H | H | $C_2H_5$ | H | H | 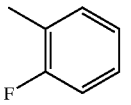 | O | $CHFCH_3$ | m.p.: 104° C. (racemate) |
| 38 | H | H | $C_2H_5$ | H | H | 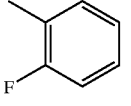 | O | $C(CH_3)_2F$ | m.p.: 113° C. (racemate) |
| 39 | H | H | $C_2H_5$ | H | H | 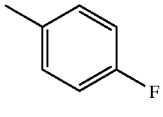 | O | $CHFCH_3$ | m.p.: 98° C. (racemate) |
| 40 | H | H | $C_2H_5$ | H | H | 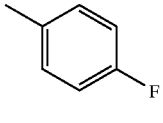 | O | $C(CH_3)_2F$ | m.p.: 99° C. (racemate) |
| 41 | H | H | $C_2H_5$ | H | H | 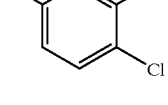 | O | $CH_2CH_3$ | m.p.: 86° C. (racemate) |
| 42 | H | H | $C_2H_5$ | H | H | 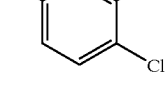 | O | $CHFCH_3$ | m.p.: 85° C. (racemate) |
| 43 | H | H | $C_2H_5$ | H | H | 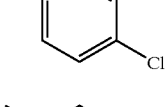 | O | $C(CH_3)_2F$ | m.p.: 97° C. (racemate) |
| 44 | H | H | $C_2H_5$ | H | H | 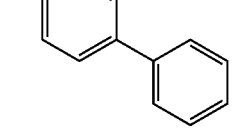 | O | $CH_2CH_3$ | m.p.: 84° C. (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 45 | H | H | $C_2H_5$ | H | H | 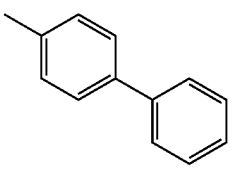 | O | $CHFCH_3$ | m.p.: 101° C. (racemate) |
| 46 | H | H | $C_2H_5$ | H | H | 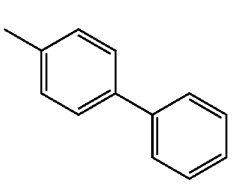 | O | $C(CH_3)_2F$ | m.p.: 89° C. (racemate) |
| 47 | H | H | $C_2H_5$ | H | H | 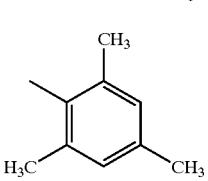 | O | $CH_2CH_3$ | (amorphous) (racemate) |
| 48 | H | H | $C_2H_5$ | H | H | 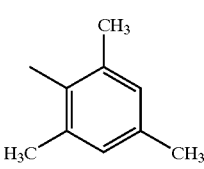 | O | $CHFCH_3$ | m.p.: 60° C. (racemate) |
| 49 | H | H | $C_2H_5$ | H | H | 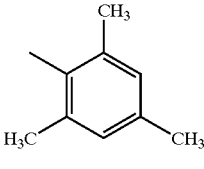 | O | $C(CH_3)_2F$ | m.p.: 63° C. (racemate) |
| 50 | H | H | $C_2H_5$ | H | H | 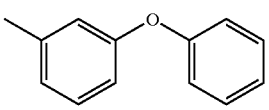 | O | $CH_2CH_3$ | (amorphous) (racemate) |
| 51 | H | H | $C_2H_5$ | H | H | 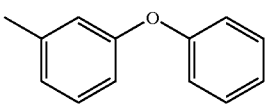 | O | $CHFCH_3$ | m.p.: 86° C. (racemate) |
| 52 | H | H | $C_2H_5$ | H | H | 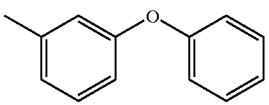 | O | $C(CH_3)_2F$ | m.p.: 91° C. (racemate) |
| 53 | H | H | $C_2H_5$ | H | H | 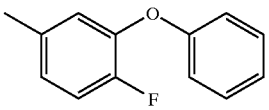 | O | $CH_2CH_3$ | (amorphous) (racemate) |
| 54 | H | H | $C_2H_5$ | H | H | 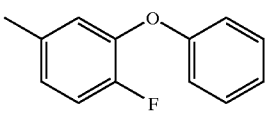 | O | $CHFCH_3$ | m.p.: 85° C. (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 55 | H | H | C₂H₅ | H | H | 2-fluoro-5-(phenoxy)phenyl | O | C(CH₃)₂F | m.p.: 116° C. (racemate) |
| 56 | H | H | C₂H₅ | H | H | 2-(trifluoromethyl)phenyl | O | CH₂CH₃ | m.p.: 83° C. (racemate) |
| 57 | H | H | C₂H₅ | H | H | 2-(trifluoromethyl)phenyl | O | CHFCH₃ | m.p.: 117° C. (racemate) |
| 58 | H | H | C₂H₅ | H | H | 2-(trifluoromethyl)phenyl | O | C(CH₃)₂F | m.p.: 131° C. (racemate) |
| 59 | H | H | C₂H₅ | H | H | 5-chlorothiophen-2-yl | O | CH₂CH₃ | m.p.: 78° C. (racemate) |
| 60 | H | H | C₂H₅ | H | H | 5-chlorothiophen-2-yl | O | CHFCH₃ | m.p.: 105° C. (racemate) |
| 61 | H | H | C₂H₅ | H | H | 5-chlorothiophen-2-yl | O | C(CH₃)₂F | m.p.: 94° C. (racemate) |
| 62 | H | H | C₂H₅ | H | H | thiophen-2-yl | O | CH₂CH₃ | (amorphous) (racemate) |
| 63 | H | H | C₂H₅ | H | H | thiophen-2-yl | O | CHFCH₃ | (amorphous) (racemate) |
| 64 | H | H | C₂H₅ | H | H | thiophen-2-yl | O | C(CH₃)₂F | (amorphous) (racemate) |
| 65 | H | H | C₂H₅ | H | H | 4-methylthiophen-2-yl | O | CH₂CH₃ | m.p.: 83° C. (racemate) |
| 66 | H | H | C₂H₅ | H | H | 4-methylthiophen-2-yl | O | CHFCH₃ | m.p.: 86° C. (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 67 | H | H | $C_2H_5$ | H | H | 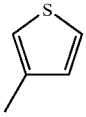 | O | $C(CH_3)_2F$ | m.p.: 94° C. (racemate) |
| 68 | H | H | $C_2H_5$ | H | H | 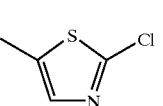 | O | $CH_2CH_3$ | |
| 69 | H | H | $C_2H_5$ | H | H | 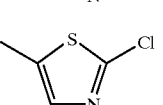 | O | $CHFCH_3$ | |
| 70 | H | H | $C_2H_5$ | H | H | 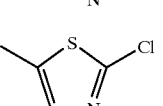 | O | $C(CH_3)_2F$ | |
| 71 | H | H | $C_2H_5$ | H | H | 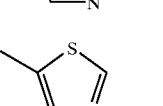 | O | $CH_2CH_3$ | |
| 72 | H | H | $C_2H_5$ | H | H | 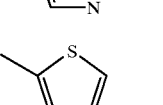 | O | $CHFCH_3$ | |
| 73 | H | H | $C_2H_5$ | H | H | 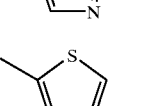 | O | $C(CH_3)_2F$ | |
| 74 | H | H | $C_2H_5$ | H | H | 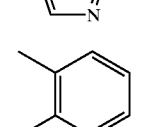 | O | $CH_2CH_3$ | m.p.: 96° C. (racemate) |
| 75 | H | H | $C_2H_5$ | H | H | 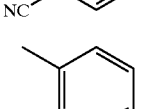 | O | $CHFCH_3$ | m.p.: 106° C. (racemate) |
| 76 | H | H | $C_2H_5$ | H | H | 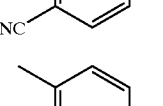 | O | $C(CH_3)_2F$ | m.p.: 119° C. (racemate) |
| 77 | H | $COCH_3$ | $CH_3$ | H | H | 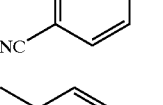 | O | $CH_2CH_3$ | |
| 78 | H | $COCH_3$ | $CH_3$ | H | H | 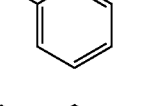 | O | $CHFCH_3$ | |
| 79 | H | $COCH_3$ | $CH_3$ | H | H | 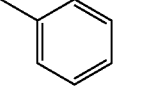 | O | $C(CH_3)_2F$ | (amorphous) (racemate) |

TABLE 1-continued

Examples of compounds of the formula (I)

| Ex. No. | R$^1$ | R$^2$ | R$^3$ | R$^4$ | R$^5$ | Ar | Q | Z | Physical data and stereochem. specifications |
|---|---|---|---|---|---|---|---|---|---|
| 80 | H | COCH$_3$ | C$_2$H$_5$ | H | H | 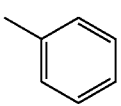 | O | CH$_2$CH$_3$ | |
| 81 | H | COCH$_3$ | C$_2$H$_5$ | H | H | 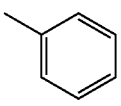 | O | CHFCH$_3$ | (amorphous) (racemate) |
| 82 | H | COCH$_3$ | C$_2$H$_5$ | H | H | 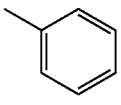 | O | C(CH$_3$)$_2$F | |
| 83 | H | COCH$_3$ | C$_2$H$_5$ | H | H | 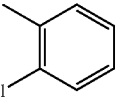 | O | CH$_2$CH$_3$ | |
| 84 | H | COCH$_3$ | C$_2$H$_5$ | H | H | 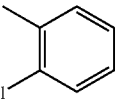 | O | CHFCH$_3$ | |
| 85 | H | COCH$_3$ | C$_2$H$_5$ | H | H | 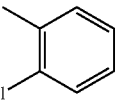 | O | C(CH$_3$)$_2$F | m.p. 102° C. (racemate) |
| 86 | H | COCH$_3$ | C$_2$H$_5$ | H | H | 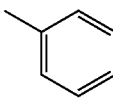 | O | CH$_2$CH$_3$ | (amorphous) (racemate) |
| 87 | H | COCH$_3$ | C$_2$H$_5$ | H | H | 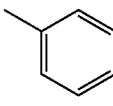 | O | CHFCH$_3$ | (amorphous) (racemate) |
| 88 | H | COCH$_3$ | C$_2$H$_5$ | H | H | 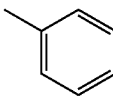 | O | C(CH$_3$)$_2$F | (amorphous) (racemate) |
| 89 | H | COCH$_3$ | C$_2$H$_5$ | H | H | 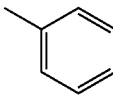 | O | CH$_2$CH$_3$ | (amorphous) (racemate) |
| 90 | H | COCH$_3$ | C$_2$H$_5$ | H | H | 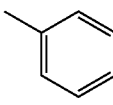 | O | CHFCH$_3$ | m.p. 104° C. (racemate) |
| 91 | H | COCH$_3$ | C$_2$H$_5$ | H | H | 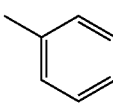 | O | C(CH$_3$)$_2$F | |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 92 | H | COCH₃ | C₂H₅ | H | H | 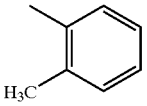 | O | CH₂CH₃ | |
| 93 | H | COCH₃ | C₂H₅ | H | H | 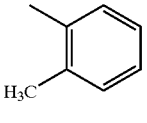 | O | CHFCH₃ | |
| 94 | H | COCH₃ | C₂H₅ | H | H | 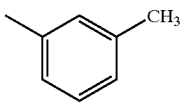 | O | CH₂CH₃ | |
| 95 | H | COCH₃ | C₂H₅ | H | H | 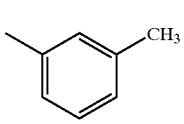 | O | CHFCH₃ | |
| 96 | H | COCH₃ | C₂H₅ | H | H | 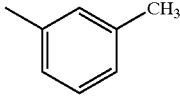 | O | C(CH₃)₂F | |
| 97 | H | COCH₃ | C₂H₅ | H | H | 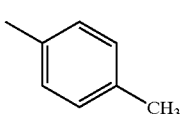 | O | CH₂CH₃ | m.p. 85° C. (racemate) |
| 98 | H | COCH₃ | C₂H₅ | H | H | 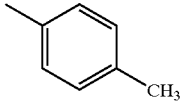 | O | CHFCH₃ | (amorphous) (racemate) |
| 99 | H | COCH₃ | C₂H₅ | H | H | 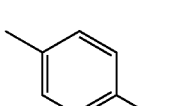 | O | C(CH₃)₂F | |
| 100 | H | COCH₃ | C₂H₅ | H | H | 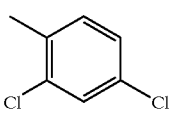 | O | CH₂CH₃ | |
| 101 | H | COCH₃ | C₂H₅ | H | H | 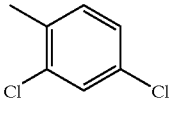 | O | CHFCH₃ | m.p. 128° C. (racemate) |
| 102 | H | COCH₃ | C₂H₅ | H | H | 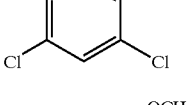 | O | C(CH₃)₂F | |
| 103 | H | COCH₃ | C₂H₅ | H | H | 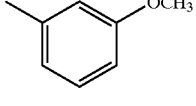 | O | CH₂CH₃ | (amorphous) (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 104 | H | COCH₃ | C₂H₅ | H | H | 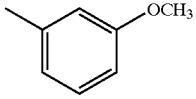 | O | CHFCH₃ | (amorphous) (racemate) |
| 105 | H | COCH₃ | C₂H₅ | H | H | 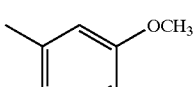 | O | C(CH₃)₂F | (amorphous) (racemate) |
| 106 | H | COCH₃ | C₂H₅ | H | H | 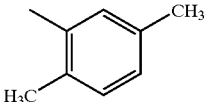 | O | CH₂CH₃ | |
| 107 | H | COCH₃ | C₂H₅ | H | H | 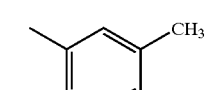 | O | CHFCH₃ | |
| 108 | H | COCH₃ | C₂H₅ | H | H | 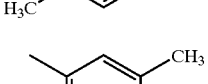 | O | C(CH₃)₂F | |
| 109 | H | COCH₃ | C₂H₅ | H | H | 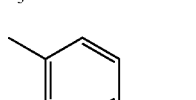 | O | CH₂CH₃ | (amorphous) (racemate) |
| 110 | H | COCH₃ | C₂H₅ | H | H | 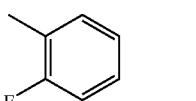 | O | CHFCH₃ | |
| 111 | H | COCH₃ | C₂H₅ | H | H | 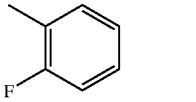 | O | C(CH₃)₂F | (amorphous) (racemate) |
| 112 | H | COCH₃ | C₂H₅ | H | H | 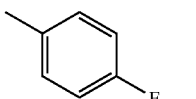 | O | CH₂CH₃ | (amorphous) (racemate) |
| 113 | H | COCH₃ | C₂H₅ | H | H | 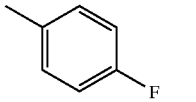 | O | CHFCH₃ | (amorphous) (racemate) |
| 114 | H | COCH₃ | C₂H₅ | H | H | 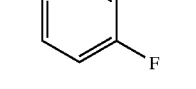 | O | C(CH₃)₂F | (amorphous) (racemate) |
| 115 | H | COCH₃ | C₂H₅ | H | H | 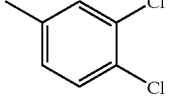 | O | CH₂CH₃ | m.p. 84° C. (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 116 | H | COCH₃ | C₂H₅ | H | H | 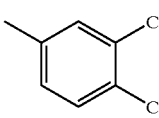 | O | CHFCH₃ | (amorphous) (racemate) |
| 117 | H | COCH₃ | C₂H₅ | H | H | 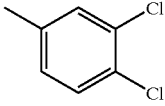 | O | C(CH₃)₂F | (amorphous) (racemate) |
| 118 | H | COCH₃ | C₂H₅ | H | H | 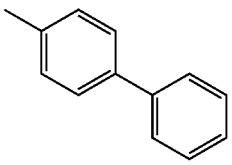 | O | CH₂CH₃ | m.p. 123° C. (racemate) |
| 119 | H | COCH₃ | C₂H₅ | H | H | 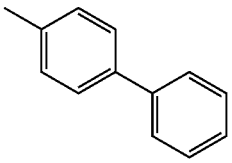 | O | CHFCH₃ | |
| 120 | H | COCH₃ | C₂H₅ | H | H | 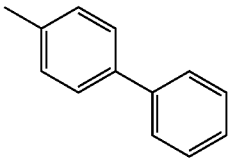 | O | C(CH₃)₂F | (amorphous) (racemate) |
| 121 | H | COCH₃ | C₂H₅ | H | H | 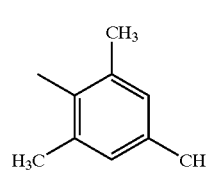 | O | CH₂CH₃ | |
| 122 | H | COCH₃ | C₂H₅ | H | H | 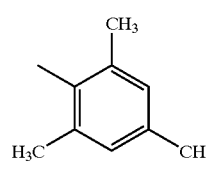 | O | CHFCH₃ | |
| 123 | H | COCH₃ | C₂H₅ | H | H | 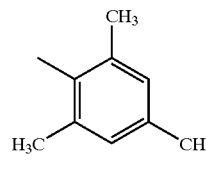 | O | C(CH₃)₂F | |
| 124 | H | COCH₃ | C₂H₅ | H | H | 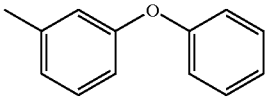 | O | CH₂CH₃ | |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 125 | H | COCH$_3$ | C$_2$H$_5$ | H | H | 3-phenoxyphenyl | O | CHFCH$_3$ | |
| 126 | H | COCH$_3$ | C$_2$H$_5$ | H | H | 3-phenoxyphenyl | O | C(CH$_3$)$_2$F | (amorphous) (racemate) |
| 127 | H | COCH$_3$ | C$_2$H$_5$ | H | H | 4-fluoro-3-phenoxyphenyl | O | CH$_2$CH$_3$ | (amorphous) (racemate) |
| 128 | H | COCH$_3$ | C$_2$H$_5$ | H | H | 4-fluoro-3-phenoxyphenyl | O | CHFCH$_3$ | (amorphous) (racemate) |
| 129 | H | COCH$_3$ | C$_2$H$_5$ | H | H | 4-fluoro-3-phenoxyphenyl | O | C(CH$_3$)$_2$F | |
| 130 | H | COCH$_3$ | C$_2$H$_5$ | H | H | 2-(trifluoromethyl)phenyl | O | CH$_2$CH$_3$ | (amorphous) (racemate) |
| 131 | H | COCH$_3$ | C$_2$H$_5$ | H | H | 2-(trifluoromethyl)phenyl | O | CHFCH$_3$ | (amorphous) (racemate) |
| 132 | H | COCH$_3$ | C$_2$H$_5$ | H | H | 2-(trifluoromethyl)phenyl | O | C(CH$_3$)$_2$F | |
| 133 | H | COCH$_3$ | C$_2$H$_5$ | H | H | 5-chlorothien-2-yl | O | CH$_2$CH$_3$ | |
| 134 | H | COCH$_3$ | C$_2$H$_5$ | H | H | 5-chlorothien-2-yl | O | CHFCH$_3$ | m.p. 83° C. (racemate) |
| 135 | H | COCH$_3$ | C$_2$H$_5$ | H | H | 5-chlorothien-2-yl | O | C(CH$_3$)$_2$F | |
| 136 | H | COCH$_3$ | C$_2$H$_5$ | H | H | 4-methylthien-2-yl | O | CH$_2$CH$_3$ | |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 137 | H | COCH₃ | C₂H₅ | H | H | 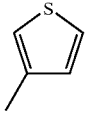 | O | CHFCH₃ | |
| 138 | H | COCH₃ | C₂H₅ | H | H | 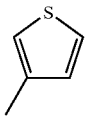 | O | C(CH₃)₂F | (amorphous) (racemate) |
| 139 | H | COCH₃ | C₂H₅ | H | H |  | O | CH₂CH₃ | |
| 140 | H | COCH₃ | C₂H₅ | H | H |  | O | CHFCH₃ | |
| 141 | H | COCH₃ | C₂H₅ | H | H | 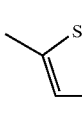 | O | C(CH₃)₂F | |
| 142 | H | COCH₃ | C₂H₅ | H | H | 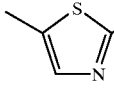 | O | CH₂CH₃ | |
| 143 | H | COCH₃ | C₂H₅ | H | H | 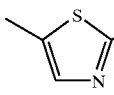 | O | CHFCH₃ | |
| 144 | H | COCH₃ | C₂H₅ | H | H | 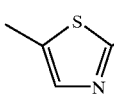 | O | C(CH₃)₂F | |
| 145 | H | COCH₃ | C₂H₅ | H | H | 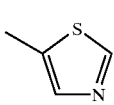 | O | CH₂CH₃ | |
| 146 | H | COCH₃ | C₂H₅ | H | H | 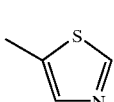 | O | CHFCH₃ | |
| 147 | H | COCH₃ | C₂H₅ | H | H | 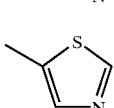 | O | C(CH₃)₂F | |
| 148 | H | COCH₃ | C₂H₅ | H | H | 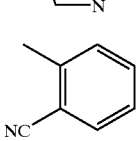 | O | CH₂CH₃ | |
| 149 | H | COCH₃ | C₂H₅ | H | H | 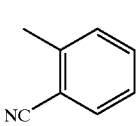 | O | CHFCH₃ | |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 150 | H | COCH₃ | C₂H₅ | H | H | 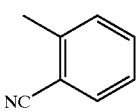 | O | C(CH₃)₂F | m.p. 131° C. (racemate) |
| 151 | H | COC₂H₅ | CH₃ | H | H |  | O | CH₂CH₃ | |
| 152 | H | COC₂H₅ | CH₃ | H | H |  | O | CHFCH₃ | |
| 153 | H | COC₂H₅ | CH₃ | H | H |  | O | C(CH₃)₂F | m.p. 126° C. (racemate) |
| 154 | H | COC₂H₅ | C₂H₅ | H | H |  | O | CH₂CH₃ | (amorphous) (racemate) |
| 155 | H | COC₂H₅ | C₂H₅ | H | H |  | O | CHFCH₃ | |
| 156 | H | COC₂H₅ | C₂H₅ | H | H |  | O | C(CH₃)₂F | |
| 157 | H | COC₂H₅ | C₂H₅ | H | H | 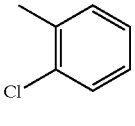 | O | CH₂CH₃ | (amorphous) (racemate) |
| 158 | H | COC₂H₅ | C₂H₅ | H | H | 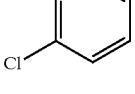 | O | CHFCH₃ | |
| 159 | H | COC₂H₅ | C₂H₅ | H | H | 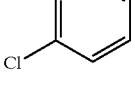 | O | C(CH₃)₂F | |
| 160 | H | COC₂H₅ | C₂H₅ | H | H | 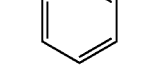 | O | CH₂CH₃ | (amorphous) (racemate) |
| 161 | H | COC₂H₅ | C₂H₅ | H | H |  | O | CHFCH₃ | |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 162 | H | COC₂H₅ | C₂H₅ | H | H | 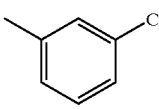 | O | C(CH₃)₂F | |
| 163 | H | COC₂H₅ | C₂H₅ | H | H | 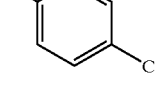 | O | CH₂CH₃ | (amorphous) (racemate) |
| 164 | H | COC₂H₅ | C₂H₅ | H | H | 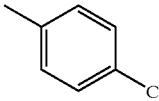 | O | CHFCH₃ | (amorphous) (racemate) |
| 165 | H | COC₂H₅ | C₂H₅ | H | H | 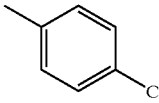 | O | C(CH₃)₂F | |
| 166 | H | COC₂H₅ | C₂H₅ | H | H | 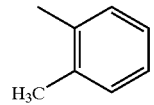 | O | CH₂CH₃ | |
| 167 | H | COC₂H₅ | C₂H₅ | H | H | 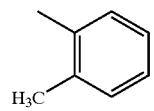 | O | CHFCH₃ | |
| 168 | H | COC₂H₅ | C₂H₅ | H | H | 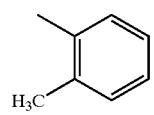 | O | C(CH₃)₂F | |
| 169 | H | COC₂H₅ | C₂H₅ | H | H | 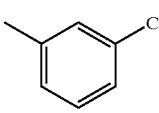 | O | CH₂CH₃ | (amorphous) (racemate) |
| 170 | H | COC₂H₅ | C₂H₅ | H | H | 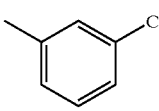 | O | CHFCH₃ | |
| 171 | H | COC₂H₅ | C₂H₅ | H | H | 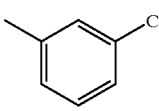 | O | C(CH₃)₂F | |
| 172 | H | COC₂H₅ | C₂H₅ | H | H | 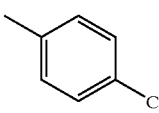 | O | CH₂CH₃ | |
| 173 | H | COC₂H₅ | C₂H₅ | H | H | 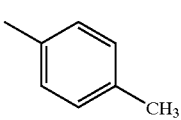 | O | CHFCH₃ | (amorphous) (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 174 | H | COC$_2$H$_5$ | C$_2$H$_5$ | H | H | 4-CH$_3$-C$_6$H$_4$ | O | C(CH$_3$)$_2$F | |
| 175 | H | COC$_2$H$_5$ | C$_2$H$_5$ | H | H | 2,4-Cl$_2$-C$_6$H$_3$ | O | CH$_2$CH$_3$ | |
| 176 | H | COC$_2$H$_5$ | C$_2$H$_5$ | H | H | 2,4-Cl$_2$-C$_6$H$_3$ | O | CHFCH$_3$ | |
| 177 | H | COC$_2$H$_5$ | C$_2$H$_5$ | H | H | 2,4-Cl$_2$-C$_6$H$_3$ | O | C(CH$_3$)$_2$F | |
| 178 | H | COC$_2$H$_5$ | C$_2$H$_5$ | H | H | 3-OCH$_3$-C$_6$H$_4$ | O | CH$_2$CH$_3$ | (amorphous) (racemate) |
| 179 | H | COC$_2$H$_5$ | C$_2$H$_5$ | H | H | 3-OCH$_3$-C$_6$H$_4$ | O | CHFCH$_3$ | |
| 180 | H | COC$_2$H$_5$ | C$_2$H$_5$ | H | H | 3-OCH$_3$-C$_6$H$_4$ | O | C(CH$_3$)$_2$F | |
| 181 | H | COC$_2$H$_5$ | C$_2$H$_5$ | H | H | 2,4-(CH$_3$)$_2$-C$_6$H$_3$ | O | CH$_2$CH$_3$ | |
| 182 | H | COC$_2$H$_5$ | C$_2$H$_5$ | H | H | 2,4-(CH$_3$)$_2$-C$_6$H$_3$ | O | CHFCH$_3$ | |
| 183 | H | COC$_2$H$_5$ | C$_2$H$_5$ | H | H | 2,4-(CH$_3$)$_2$-C$_6$H$_3$ | O | C(CH$_3$)$_2$F | |
| 184 | H | COC$_2$H$_5$ | C$_2$H$_5$ | H | H | 2-F-C$_6$H$_4$ | O | CH$_2$CH$_3$ | |
| 185 | H | COC$_2$H$_5$ | C$_2$H$_5$ | H | H | 2-F-C$_6$H$_4$ | O | CHFCH$_3$ | |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 186 | H | COC₂H₅ | C₂H₅ | H | H | 2-F-C₆H₄ | O | C(CH₃)₂F | |
| 187 | H | COC₂H₅ | C₂H₅ | H | H | 4-F-C₆H₄ | O | CH₂CH₃ | |
| 188 | H | COC₂H₅ | C₂H₅ | H | H | 4-F-C₆H₄ | O | CHFCH₃ | |
| 189 | H | COC₂H₅ | C₂H₅ | H | H | 4-F-C₆H₄ | O | C(CH₃)₂F | |
| 190 | H | COC₂H₅ | C₂H₅ | H | H | 3,4-Cl₂-C₆H₃ | O | CH₂CH₃ | |
| 191 | H | COC₂H₅ | C₂H₅ | H | H | 3,4-Cl₂-C₆H₃ | O | CHFCH₃ | |
| 192 | H | COC₂H₅ | C₂H₅ | H | H | 3,4-Cl₂-C₆H₃ | O | C(CH₃)₂F | |
| 193 | H | COC₂H₅ | C₂H₅ | H | H | 4-biphenyl | O | CH₂CH₃ | |
| 194 | H | COC₂H₅ | C₂H₅ | H | H | 4-biphenyl | O | CHFCH₃ | |
| 195 | H | COC₂H₅ | C₂H₅ | H | H | 4-biphenyl | O | C(CH₃)₂F | |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 196 | H | COC$_2$H$_5$ | C$_2$H$_5$ | H | H | 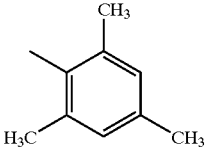 | O | CH$_2$CH$_3$ | |
| 197 | H | COC$_2$H$_5$ | C$_2$H$_5$ | H | H | 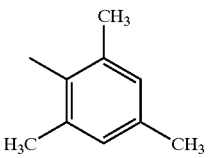 | O | CHFCH$_3$ | |
| 198 | H | COC$_2$H$_5$ | C$_2$H$_5$ | H | H | 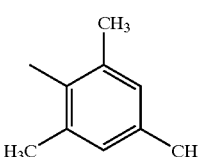 | O | C(CH$_3$)$_2$F | |
| 199 | H | COC$_2$H$_5$ | C$_2$H$_5$ | H | H | 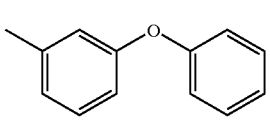 | O | CH$_2$CH$_3$ | |
| 200 | H | COC$_2$H$_5$ | C$_2$H$_5$ | H | H | 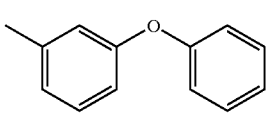 | O | CHFCH$_3$ | |
| 201 | H | COC$_2$H$_5$ | C$_2$H$_5$ | H | H | 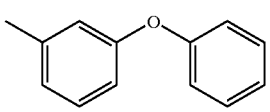 | O | C(CH$_3$)$_2$F | |
| 202 | H | COC$_2$H$_5$ | C$_2$H$_5$ | H | H | 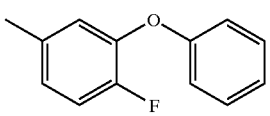 | O | CH$_2$CH$_3$ | |
| 203 | H | COC$_2$H$_5$ | C$_2$H$_5$ | H | H | 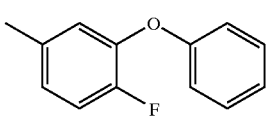 | O | CHFCH$_3$ | |
| 204 | H | COC$_2$H$_5$ | C$_2$H$_5$ | H | H | 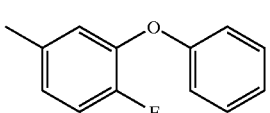 | O | C(CH$_3$)$_2$F | |
| 205 | H | COC$_2$H$_5$ | C$_2$H$_5$ | H | H | 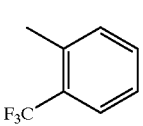 | O | CH$_2$CH$_3$ | |
| 206 | H | COC$_2$H$_5$ | C$_2$H$_5$ | H | H | 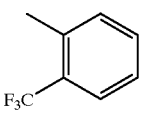 | O | CHFCH$_3$ | |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 207 | H | COC$_2$H$_5$ | C$_2$H$_5$ | H | H | 2-(trifluoromethyl)phenyl | O | C(CH$_3$)$_2$F | |
| 208 | H | COC$_2$H$_5$ | C$_2$H$_5$ | H | H | 5-chlorothiophen-2-yl | O | CH$_2$CH$_3$ | (amorphous) (racemate) |
| 209 | H | COC$_2$H$_5$ | C$_2$H$_5$ | H | H | 5-chlorothiophen-2-yl | O | CHFCH$_3$ | |
| 210 | H | COC$_2$H$_5$ | C$_2$H$_5$ | H | H | 5-chlorothiophen-2-yl | O | C(CH$_3$)$_2$F | |
| 211 | H | COC$_2$H$_5$ | C$_2$H$_5$ | H | H | thiophen-2-yl | O | CH$_2$CH$_3$ | |
| 212 | H | COC$_2$H$_5$ | C$_2$H$_5$ | H | H | thiophen-2-yl | O | CHFCH$_3$ | |
| 213 | H | COC$_2$H$_5$ | C$_2$H$_5$ | H | H | thiophen-2-yl | O | C(CH$_3$)$_2$F | |
| 214 | H | COC$_2$H$_5$ | C$_2$H$_5$ | H | H | thiophen-3-yl | O | CH$_2$CH$_3$ | |
| 215 | H | COC$_2$H$_5$ | C$_2$H$_5$ | H | H | thiophen-3-yl | O | CHFCH$_3$ | |
| 216 | H | COC$_2$H$_5$ | C$_2$H$_5$ | H | H | thiophen-3-yl | O | C(CH$_3$)$_2$F | |
| 217 | H | COC$_2$H$_5$ | C$_2$H$_5$ | H | H | 2-chlorothiazol-5-yl | O | CH$_2$CH$_3$ | |
| 218 | H | COC$_2$H$_5$ | C$_2$H$_5$ | H | H | 2-chlorothiazol-5-yl | O | CHFCH$_3$ | |
| 219 | H | COC$_2$H$_5$ | C$_2$H$_5$ | H | H | 2-chlorothiazol-5-yl | O | C(CH$_3$)$_2$F | |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 220 | H | COC$_2$H$_5$ | C$_2$H$_5$ | H | H | 5-thiazolyl | O | CH$_2$CH$_3$ | |
| 221 | H | COC$_2$H$_5$ | C$_2$H$_5$ | H | H | 5-thiazolyl | O | CHFCH$_3$ | |
| 222 | H | COC$_2$H$_5$ | C$_2$H$_5$ | H | H | 5-thiazolyl | O | C(CH$_3$)$_2$F | |
| 223 | H | COC$_2$H$_5$ | C$_2$H$_5$ | H | H | 2-CN-phenyl | O | CH$_2$CH$_3$ | |
| 224 | H | COC$_2$H$_5$ | C$_2$H$_5$ | H | H | 2-CN-phenyl | O | CHFCH$_3$ | |
| 225 | H | COC$_2$H$_5$ | C$_2$H$_5$ | H | H | 2-CN-phenyl | O | C(CH$_3$)$_2$F | |
| 226 | H | H | CH$_3$ | H | H | 3,4,5-trimethylisoxazolyl | O | CF$_3$ | |
| 227 | H | H | CH$_3$ | H | H | phenyl | S | C(CH$_3$)$_2$F | $n_{20}^D$: 1.5635 (racemate) |
| 228 | H | H | CH$_3$ | H | H | phenyl | SO$_2$ | C(CH$_3$)$_2$F | m.p.: 67° C. (racemate) |
| 229 | H | H | C$_2$H$_5$ | H | H | phenyl | S | C(CH$_3$)$_2$F | |
| 230 | H | H | C$_2$H$_5$ | H | H | 3-Cl-6-F-phenyl | O | C$_2$H$_5$ | m.p.: 69° C. racemate |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 231 | H | H | $C_2H_5$ | H | H | 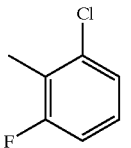 | O | $CHFCH_3$ | (amorphous) (racemate) |
| 232 | H | H | $C_2H_5$ | H | H | 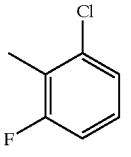 | O | $CF(CH_3)_2$ | (amorphous) (racemate) |
| 233 | H | H | $C_2H_5$ | H | H | 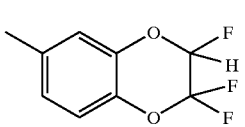 | O | $C_2H_5$ | m.p.: 84° C. (racemate) |
| 234 | H | H | $C_2H_5$ | H | H | 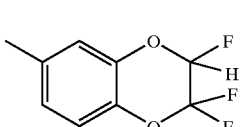 | O | $CHFCH_3$ | (amorphous) (racemate) |
| 235 | H | H | $C_2H_5$ | H | H | 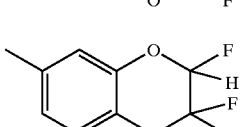 | O | $CF(CH_3)_2$ | m.p.: 99° C. (racemate) |
| 236 | H | H | $C_2H_5$ | H | H | 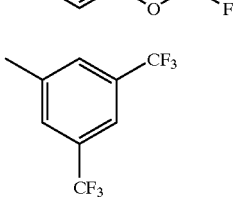 | O | $CF(CH_3)_2$ | m.p.: 61° C. (racemate) |
| 237 | H | H | $C_2H_5$ | H | H | 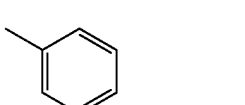 | O | $C_2H_5$ | m.p.: 87° C. (S enantiomer) |
| 238 | H | H | $C_2H_5$ | H | H | 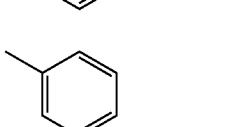 | O | $CHFCH_3$ | m.p.: 98° C. (S enantiomer) |
| 239 | H | H | $C_2H_5$ | H | H | 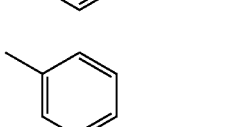 | O | $CF(CH_3)_2$ | m.p.: 89° C. (S enantiomer) |
| 240 | H | H | $C_2H_5$ | H | H | 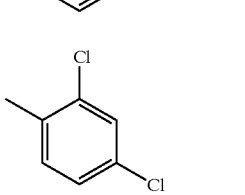 | O | $C_2H_5$ | m.p.: 111° C. (R enantiomer) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 241 | H | H | C₂H₅ | H | H | 2,4-dichlorophenyl | O | CHFCH₃ | m.p.: 99° C. (R enantiomer) |
| 242 | H | H | C₂H₅ | H | H | 2,4-dichlorophenyl | O | CF(CH₃)₂ | m.p.: 117° C. (R enantiomer) |
| 243 | H | H | C₂H₅ | H | H | 3-chloro-4-methylphenyl | O | CF(CH₃)₂ | m.p.: 80° C. (racemate) |
| 244 | H | H | C₂H₅ | H | H | 3-chloro-4-methylphenyl | O | C₂H₅ | m.p.: 64° C. (racemate) |
| 245 | H | H | C₂H₅ | H | H | 2-chloro-3-methylphenyl | O | CF(CH₃)₂ | m.p.: 85° C. (racemate) |
| 246 | H | H | C₂H₅ | H | H | 2-chloro-3-methylphenyl | O | CHFCH₃ | m.p.: 112° C. (racemate) |
| 247 | H | H | C₂H₅ | H | H | 2-chloro-3-methylphenyl | O | C₂H₅ | m.p.: 118° C. (racemate) |
| 248 | H | H | CH₃ | H | H | phenyl | O | CF(CH₃)₂ | m.p.: 84° C. (S enantiomer) |
| 249 | H | H | CH₃ | H | H | phenyl | O | C₂H₅ | m.p.: 61° C. (S enantiomer) |
| 250 | H | H | CH₃ | H | H | phenyl | O | CF(CH₃)₂ | m.p.: 82° C. (R enantiomer) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 251 | H | H | CH₃ | H | H |  | O | C₂H₅ | m.p.: 73° C. (R enantiomer) |
| 252 | H | H | C₂H₅ | H | H | 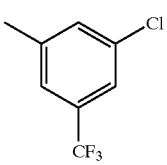 | O | CF(CH₃)₂ | m.p.: 96° C. (racemate) |
| 253 | H | H | C₂H₅ | H | H | 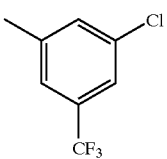 | O | CHFCH₃ | m.p.: 96° C. (racemate) |
| 254 | H | H | C₂H₅ | H | H |  | O | CF(CH₃)₂ | (amorphous) (S enantiomer) |
| 255 | H | H | C₂H₅ | H | H | 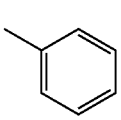 | O | CHFCH₃ | m.p.: 97° C. (S enantiomer) |
| 256 | H | H | CH₃ | H | H | 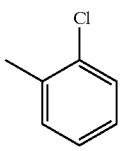 | O | CF(CH₃)₂ | m.p.: 95° C. (racemate) |
| 257 | H | H | CH₃ | H | H | 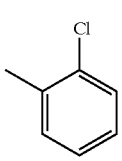 | O | CHFCH₃ | m.p.: 92° C. (racemate) |
| 258 | H | H | CH₃ | H | H | 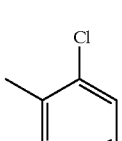 | O |  | (amorphous) (racemate) |
| 259 | H | H | CH₃ | H | H | 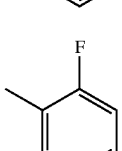 | O | CHFCH₃ | m.p.: 93° C. (racemate) |
| 260 | H | H | CH₃ | H | H | 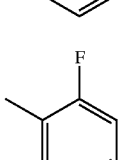 | O | CF(CH₃)₂ | m.p.: 113° C. (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 261 | H | H | CH₃ | H | H | 2-F-C₆H₄ | O | CH(CH₃)(OH) | (amorphous) (racemate) |
| 262 | H | H | C₂H₅ | H | H | 3-CH₃-5-OCH₃-C₆H₃ | O | CF(CH₃)₂ | m.p.: 98° C. (racemate) |
| 263 | H | H | CH₃ | H | H | 2,4-Cl₂-C₆H₃ | O | CF(CH₃)₂ | m.p.: 107° C. (racemate) |
| 264 | H | H | C₂H₅ | H | H | 3,5-(OCH₃)₂-C₆H₃ | O | CF(CH₃)₂ | m.p.: 100° C. (racemate) |
| 265 | H | H | C₂H₅ | H | H | 5,6,7,8-tetrahydronaphth-2-yl | O | CF(CH₃)₂ | m.p.: 117° C. (racemate) |
| 266 | H | H | C₂H₅ | H | H | 5,6,7,8-tetrahydronaphth-2-yl | O | CHFCH₃ | m.p.: 103° C. (racemate) |
| 267 | H | H | C₂H₅ | H | H | benzo[1,3]dioxol-5-yl | O | CF(CH₃)₂ | m.p.: 128° C. (racemate) |
| 268 | H | H | C₂H₅ | H | H | benzo[1,3]dioxol-5-yl | O | CHFCH₃ | m.p.: 97° C. (racemate) |
| 269 | H | H | C₂H₅ | H | H | benzo[1,3]dioxol-5-yl | O | CH(CH₃)(OH) | m.p.: 106° C. (racemate) |

TABLE 1-continued

Examples of compounds of the formula (I)

| Ex. No. | R¹ | R² | R³ | R⁴ | R⁵ | Ar | Q | Z | Physical data and stereochem. specifications |
|---|---|---|---|---|---|---|---|---|---|
| 270 | H | H | $C_2H_5$ | H | H | 2-F-C₆H₄-CH₂- | O | $CF_2Cl$ | m.p.: 100° C. (racemate) |
| 271 | H | H | $C_2H_5$ | H | H | 2-F-C₆H₄-CH₂- | O | $CHFCF_3$ | m.p.; 117° C. (racemate) |
| 272 | H | R | $C_2H_5$ | H | H | 2-F-C₆H₄-CH₂- | O | $CHCl_2$ | m.p.: 87° C. (racemate) |

Starting Materials of the Formula (II)

Example (II-1)

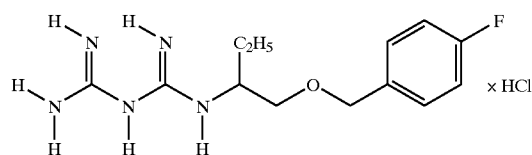

2.52 g (30 mmol) of cyanoguanidine and 7.01 g (30 mmol) of 2-amino-1-(4-fluorobenzyloxy)-butane hydrochloride (racemic) are mixed intimately in a mortar and then melted together at 160° C. for 30 minutes. During cooling, the mixture is admixed with 30 ml of methanol. The resulting solution of 1-[1-(4-fluoro-benzyloxymethyl)-propyl]-biguanide hydrochloride is reacted according to Example 1.

Analogously to Example (II-1), it is also possible to prepare, for example, the compounds of the formula (II) below.

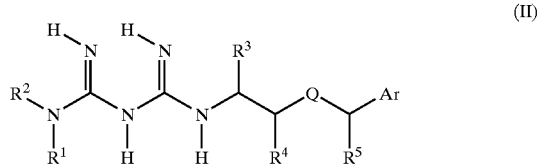

(II)

TABLE 2

Examples of compounds of the formula (II)

| Ex. No. | R³ | R⁴ | R⁵ | Ar | Q | Physical data and stereochem. specifications |
|---|---|---|---|---|---|---|
| II-2 | $CH_3$ | H | H | C₆H₅- | O | (amorphous) (racemate) |
| II-3 | $CH_2CH_3$ | H | H | C₆H₅- | O | (amorphous) (racemate) |

TABLE 2-continued

Examples of compounds of the formula (II)

| Ex. No. | R³ | R⁴ | R⁵ | Ar | Q | Physical data and stereochem. specifications |
|---|---|---|---|---|---|---|
| II-4 | CH₂CH₃ | H | H | 2-Cl-C₆H₄ | O | (amorphous) (racemate) |
| II-5 | CH₂CH₃ | H | H | 3-Cl-C₆H₄ | O | (amorphous) (racemate) |
| II-6 | CH₂CH₃ | H | H | 4-Cl-C₆H₄ | O | (amorphous) (racemate) |
| II-7 | CH₂CH₃ | H | H | 2-CH₃-C₆H₄ | O | (amorphous) (racemate) |
| II-8 | CH₂CH₃ | H | H | 3-CH₃-C₆H₄ | O | (amorphous) (racemate) |
| II-9 | CH₂CH₃ | H | H | 4-CH₃-C₆H₄ | O | (amorphous) (racemate) |
| II-10 | CH₂CH₃ | H | H | 2,4-Cl₂-C₆H₃ | O | (amorphous) (racemate) |
| II-11 | CH₂CH₃ | H | H | 3-OCH₃-C₆H₄ | O | (amorphous) (racemate) |
| II-12 | CH₂CH₃ | H | H | 2,4-(CH₃)₂-C₆H₃ | O | (amorphous) (racemate) |
| II-13 | CH₂CH₃ | H | H | 2-F-C₆H₄ | O | (amorphous) (racemate) |
| II-14 | CH₂CH₃ | H | H | 3,4-Cl₂-C₆H₃ | O | (amorphous) (racemate) |
| II-15 | CH₂CH₃ | H | H | 4-C₆H₅-C₆H₄ | O | (amorphous) (racemate) |

TABLE 2-continued

Examples of compounds of the formula (II)

| Ex. No. | R³ | R⁴ | R⁵ | Ar | Q | Physical data and stereochem. specifications |
|---|---|---|---|---|---|---|
| II-16 | CH₂CH₃ | H | H | 2,3,5-trimethylphenyl | O | (amorphous) (racemate) |
| II-17 | CH₂CH₃ | H | H | 3-phenoxyphenyl | O | (amorphous) (racemate) |
| II-18 | CH₂CH₃ | H | H | 4-fluoro-3-phenoxyphenyl | O | (amorphous) (racemate) |
| II-19 | CH₂CH₃ | H | H | 2-(trifluoromethyl)phenyl | O | (amorphous) (racemate) |
| II-20 | CH₂CH₃ | H | H | 5-chlorothiophen-2-yl | O | (amorphous) (racemate) |
| II-21 | CH₂CH₃ | H | H | thiophen-2-yl | O | (amorphous) (racemate) |
| II-22 | CH₂CH₃ | H | H | thiophen-3-yl | O | (amorphous) (racemate) |
| II-23 | CH₂CH₃ | H | H | 2-chlorothiazol-5-yl | O | |
| II-24 | CH₂CH₃ | H | H | thiazol-5-yl | O | |
| II-25 | CH₂CH₃ | H | H | 2-cyanophenyl | O | (amorphous) (racemate) |

In each case, R¹ and R² represent H (hydrogen).
All compounds are hydrochlorides.

Starting Materials of the Formula (VII)

Example (VII-1)

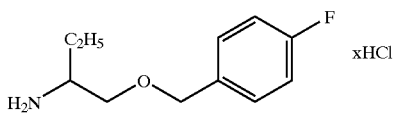

Step 1

At room temperature (about 20° C.), a solution of 7.5 ml (80 mmol) of 2-amino-1-butanol in 90 ml of tetrahydrofuran is admixed a little at a time with 2.4 g (80 mmol) of sodium hydride (80% strength) and then heated under reflux for 30 minutes. After cooling, 10.3 g (71 mmol) of 4-fluoro-benzyl chloride are added and the mixture is heated under reflux for 2 hours. Again after cooling, water is added until the precipitated salt has dissolved, and the solvent is distilled off from the mixture under water pump vacuum. The residue is poured into 1N hydrochloric acid and extracted twice with dichloromethane. The dichloromethane phase is reextracted with water. The aqueous phase is then adjusted to pH 10 using conc. aqueous sodium hydroxide solution and extracted three times with dichloromethane. The organic extract solution is dried over sodium sulphate and filtered. From the filtrate, the solvent is carefully distilled off under water pump vacuum.

This gives 13.4 g (96% of theory) of 2-amino-1-(4-fluorobenzyloxy)-butane as an oily residue.

Step 2

13.4 g (68 mmol) of 2-amino-1-(4-fluorobenzyloxy) butane are dissolved in 40 ml of methanol and admixed with 7.7 g (68 mmol) of conc. hydrochloric acid. The solvent is removed under water pump vacuum and the residue is admixed with 20 ml of toluene and once more concentrated under water pump vacuum.

This gives 14.9 g (94% of theory) of 2-amino-1-(4-fluorobenzyloxy)-butane hydrochloride as a white solid.

Analogously to Example (VII-1), it is also possible to prepare, for example, the compounds of the formula (VII) listed in Table 3 below.

(VII)

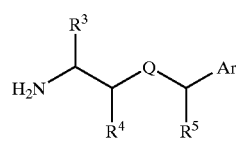

TABLE 3

| | Examples of compounds of the formula (VII) | | | | | |
|---|---|---|---|---|---|---|
| Ex. No. | $R^3$ | $R^4$ | $R^5$ | Ar | Q | Physical data and stereochem. specifications |
| VII-2 | $CH_2CH_3$ | H | H | 2-Cl-C6H4 | O | m.p.: 141° C. (racemate) |
| VII-3 | $CH_2CH_3$ | H | H | 3-Cl-C6H4 | O | m.p.: 97° C. (racemate) |
| VII-4 | $CH_2CH_3$ | H | H | 2-CH3-C6H4 | O | m.p.: 112° C. (racemate) |
| VII-5 | $CH_2CH_3$ | H | H | 3-CH3-C6H4 | O | m.p.: 101° C. (racemate) |
| VII-6 | $CH_2CH_3$ | H | H | 4-CH3-C6H4 | O | m.p.: 115° C. (racemate) |

TABLE 3-continued

Examples of compounds of the formula (VII)

| Ex. No. | R³ | R⁴ | R⁵ | Ar | Q | Physical data and stereochem. specifications |
|---|---|---|---|---|---|---|
| VII-7 | CH₂CH₃ | H | H | 3-OCH₃-phenyl | O | m.p.: 103° C. (racemate) |
| VII-8 | CH₂CH₃ | H | H | 2,5-dimethyl-phenyl (with 2-CH₃ shown as H₃C) — 2,4-di-CH₃ phenyl | O | m.p.: 113° C. (racemate) |
| VII-9 | CH₂CH₃ | H | H | 2-F-phenyl | O | m.p.: 129° C. (racemate) |
| VII-10 | CH₂CH₃ | H | H | 3,4-di-Cl-phenyl | O | m.p.: 145° C. (racemate) |
| VII-11 | CH₂CH₃ | H | H | 4-biphenyl | O | m.p.: 150° C. (racemate) |
| VII-12 | CH₂CH₃ | H | H | 2,4,6-tri-CH₃-phenyl | O | m.p.: 78° C. (racemate) |
| VII-13 | CH₂CH₃ | H | H | 3-phenoxy-phenyl | O | m.p.: 66° C. (racemate) |
| VII-14 | CH₂CH₃ | H | H | 4-F-3-phenoxy-phenyl | O | m.p.: 125° C. (racemate) |
| VII-15 | CH₂CH₃ | H | H | 2-CF₃-phenyl | O | m.p.: 84° C. (racemate) |
| VII-16 | CH₂CH₃ | H | H | 5-Cl-thien-2-yl | O | m.p.: 63° C. (racemate) |

TABLE 3-continued

Examples of compounds of the formula (VII)

| Ex. No. | R³ | R⁴ | R⁵ | Ar | Q | Physical data and stereochem. specifications |
|---|---|---|---|---|---|---|
| VII-17 | CH₂CH₃ | H | H | 2-thienyl | O | m.p.: 58° C. (racemate) |
| VII-18 | CH₂CH₃ | H | H | 3-methyl-thienyl | O | m.p.: 72° C. (racemate) |
| VII-19 | CH₂CH₃ | H | H | 2-chloro-thiazolyl | O | |
| VII-20 | CH₂CH₃ | H | H | thiazolyl | O | |
| VII-21 | CH₂CH₃ | H | H | 2-cyanophenyl | O | m.p.: 93° C. (racemate) |
| VII-22 | CH₂CH₃ | H | H | 2-chloro-3-fluorophenyl | O | |
| VII-23 | CH₂CH₃ | H | H | 3,5-bis(trifluoromethyl)phenyl | O | |
| VII-24 | CH₂CH₃ | H | H | 3-trifluoro-benzodioxine | O | |

The compounds are in each case the hydrochlorides

USE EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison with the development of the untreated control.

The figures denote:

0%=no effect (like untreated control)

100%=total destruction

In this test, for example, the compounds of Preparation Examples 8 and 14 exhibit very strong action against weeds (cf. Table A; "ai."=active ingredient), and some of them are tolerated well by crop plants, such as, for example, maize.

TABLE A

Pre-emergence test (greenhouse)

| Active compound of Preparation Example No. | Application rate (g of ai.ha) | Alopecurus | Setaria | Abutilon | Amaranthus | Galium | Sinapis |
|---|---|---|---|---|---|---|---|
| 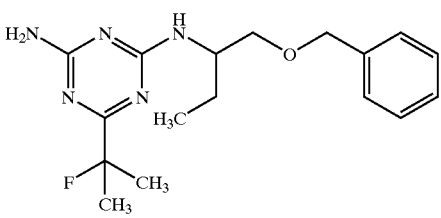 (8) | 1000 | 100 | 100 | 100 | 100 | 100 | 100 |

| Active compound of Preparation Example No. | Application rate (g of ai./ha) | Maize | Alopecurus | Abutilon | Amaranthus | Sinapis |
|---|---|---|---|---|---|---|
| 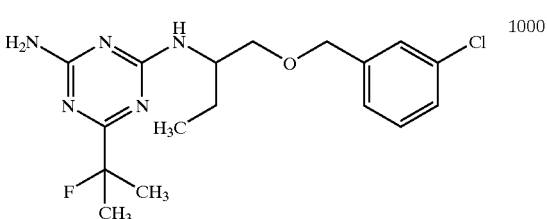 (14) | 1000 | 10 | 95 | 95 | 100 | 90 |

Example B

Post-emergence Test

Solvent: 5 parts by weight of acetone

Emulsifier: 1 part by weight of alkylaryl polyglycol ether

To produce a suitable preparation of active compound, l part by weight of active compound is mixed with the stated amount of solvent, the stated amount of emulsifier is added and the concentrate is diluted with water to the desired concentration.

Test plants having a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison with the development of the untreated control.

The figures denote:

0%=no effect (like untreated control)

100%=total destruction

In this test, for example, the compounds of Preparation Example 8 and 14 exhibit very strong action against weeds (cf. Table B).

TABLE B

Post-emergence test/greenhouse

| Active ingredient of Preparation Example No. | Application rate (g of ai./ha) | Alopecurus | Abutilon | Amaranthus | Galium | Sinapis |
|---|---|---|---|---|---|---|
| 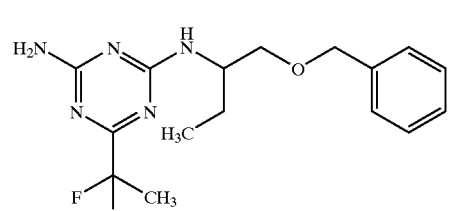 (8) | 1000 | 95 | 100 | 100 | 90 | 100 |

TABLE B-continued

Post-emergence test/greenhouse

| Active ingredient of Preparation Example No. | Application rate (g of ai./ha) | Alopecurus | Abutilon | Amaranthus | Galium | Sinapis |
|---|---|---|---|---|---|---|
| 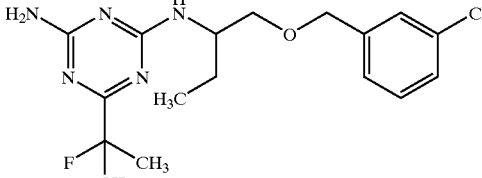 (14) | 1000 | 100 | 100 | 100 | 95 | 100 |

What is claimed is:

1. A compound of the formula (I)

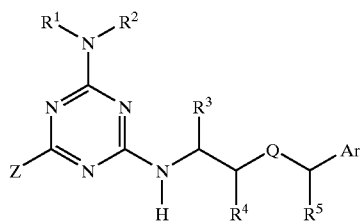

wherein

Q represents O, S, SO, $SO_2$, NH or $N(C_1-C_4$-alkyl), $R^1$ represents hydrogen or represents unsubstituted or hydroxyl-, cyano-, halogen- or $C_1-C_4$-alkoxy-substituted alkyl having 1 to 6 carbon atoms, $R^2$ represents hydrogen, represents formyl or represents in each case unsubstituted or cyano-, halogen- or $C_1-C_4$-alkoxy-substituted alkyl, alkylcarbonyl, alkoxycarbonyl or alkylaminocarbonyl having in each case 1 to 6 carbon atoms in the alkyl groups, $R^3$ represents unsubstituted or hydroxyl-, cyano-, halogen- or $C_1-C_4$-alkoxy-substituted alkyl having 1 to 6 carbon atoms or represents unsubstituted or cyano-, halogen- or $C_1-C_4$-alkyl-substituted cycloalkyl having 3 to 6 carbon atoms, $R^4$ represents hydrogen or alkyl having 1 to 4 carbon atoms, $R^5$ represents hydrogen or alkyl having 1 to 4 carbon atoms, Ar represents in each case unsubstituted or substituted phenyl, naphthyl, tetralinyl or heteroaryl, wherein the heteroaryl is selected from the group consisting of:

furyl, benzofuryl, thienyl, benzothienyl, thiazolyl, benzothiazolyl, oxazolyl, benzoxazolyl, isoxazolyl, thiadiazolyl, oxadiazolyl, pyrazolyl, imidazolyl, pyrrolyl, pyridinyl, and pyrimidinyl, and wherein the substituent are in each case selected from the group consisting of:

hydroxyl, cyano, carbamoyl, thiocarbamoyl, nitro, halogen; unsubstituted or hydroxyl-, cyano- or halogen-substituted alkyl or alkoxy having in each case 1 to 6 carbon atoms; unsubstituted or halogen-substituted alkylcarbonyl, alkoxycarbonyl, alkylthio, alkylsulphinyl, alkylsulphonyl, dialkylamino, alkylcarbonylamino, alkylsulphonyl-amino, bis-alkylcarbonyl-amino, bis-alkylsulphonyl-amino, N-alkyl-N-alkylcarbonyl-amino or N-alkyl-N-alkylsulphonyl-amino having in each case 1 to 6 carbon atoms in the alkyl groups; unsubstituted or hydroxyl-, cyano-, nitro-, halogen-, $C_1-C_4$-alkyl-, $C_1-C_4$-halogenoalkyl-, $C_1-C_4$-alkoxy- or $C_1-C_4$-halogenoalkoxy-substituted phenyl or phenoxy; and unsubstituted or halogen-substituted methylenedioxy or ethylenedioxy, and Z is selected from the group consisting of hydrogen, cyano, halogen; unsubstituted or hydroxyl-, cyano-, halogen-, $C_1-C_4$-alkoxy-, $C_1-C_4$-alkyl-carbonyl-, $C_1-C_4$-alkoxy-carbonyl-, $C_1-C_4$-alkylthio-, $C_1-C_4$-alkylsulphinyl- or $C_1-C_4$-alkylsulphonyl-substituted alkyl, alkoxy, alkylcarbonyl, alkoxycarbonyl, alkylthio, alkylsulphinyl or alkylsulphonyl having in each case 1 to 6 carbon atoms in the alkyl groups: unsubstituted or cyano-, halogen- or $C_1-C_4$-alkoxy-substituted alkenyl or alkynyl having in each case 2 to 4 carbon atoms in the alkenyl or alkynyl group; and unsubstituted or cyano-, halogen- or $C_1-C_4$-alkyl-substituted cycloalkyl having 3 to 6 carbon atoms.

2. The compound of claim 1, wherein

Q represents O, S or NH, $R^1$ represents hydrogen or represents unsubstituted or hydroxyl-, cyano-, fluorine-, chlorine-, methoxy- or ethoxy-substituted methyl, ethyl, n- or i-propyl, n-, i-, s- or t-butyl, $R^2$ represents hydrogen, represents formyl, or represents unsubstituted or cyano-, fluorine-, chlorine-, bromine-, methoxy- or ethoxy-substituted methyl, ethyl, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, $R^3$ represents unsubstituted or hydroxyl-, cyano-, fluorine-, chlorine-, methoxy- or ethoxy-substituted ethyl, n- or i-propyl, n-, i-, s- or t-butyl; or unsubstituted or cyano-, fluorine-, chlorine-, methyl- or ethyl-substituted cyclopropyl, cyclobutyl, cyclopentyl or cyclohexyl, $R^4$ represents hydrogen or methyl, $R^5$ represents hydrogen or methyl, Ar represents unsubstituted or substituted phenyl, naphthyl, tetralinyl or heteroaryl, wherein the heteroaryl is selected from the group consisting of:

furyl, benzofuryl, thienyl, benzothienyl, thiazolyl, benzothiazolyl, oxazolyl, benzoxazolyl, isoxazolyl, thiadiazolyl, oxadiazolyl, pyrazolyl, imidazolyl, pyrrolyl, pyridinyl, and pyrimidinyl, and wherein the substituents are selected from the group consisting of:

hydroxyl, cyano, carbamoyl, thiocarbamoyl, nitro, fluorine, chlorine, bromine; unsubstituted or hydroxyl-, cyano-, fluorine- or chlorine-substituted methyl, ethyl, n- or i-propyl, n-, i-, s- or t-butyl, methoxy, ethoxy, n- or i-propoxy, n-, i-, s- or t-butoxy; unsubstituted or fluorine- or chlorine-substituted acetyl, propionyl, n- or i-butyroyl, methoxycarbonyl, ethoxycarbonyl, n- or i-propoxycarbonyl, methylthio, ethylthio, n- or i-propylthio, methylsulphinyl, ethylsulphinyl, n- or i-propylsulphinyl, methylsulphonyl, ethylsulphonyl, n- or i-propylsulphonyl, dimethylamino, diethylamino, acetylamino, propionylamino, methylsulphonylamino, ethylsulphonylamino, bis-acetylamino, bis-methylsulphonyl-amino, N-methyl-N-acetyl-amino or N-methyl-N-methylsulphonyl-amino; unsubstituted or hydroxyl-, cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl or phenoxy; and unsubstituted or fluorine- or chlorine-substituted methylenedioxy or ethylenedioxy; and Z is selected from the group consisting of represents fluorine, chlorine, bromine; unsubstituted or hydroxyl-, cyano-, nitro-, fluorine-, chlorine-, methoxy-, ethoxy-, n- or i-propoxy-, n-, i-, s- or t-butoxy-, methylthio-, ethylthio-, n- or i-propylthio-, methylsulphinyl-, ethylsulphinyl-, n- or i-propylsulphinyl-, methylsulphonyl-, ethylsulphonyl-, n- or i-propylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, methylsulphinyl, ethylsulphinyl, n- or i-propylsulphinyl, methylsulphonyl, ethylsulphonyl, n- or i-propylsulphonyl; unsubstituted or cyano-, fluorine-, chlorine-, bromine-, methoxy- or ethoxy-substituted ethenyl, propenyl, butenyl, ethinyl, propinyl or butinyl; and unsubstituted or cyano-, fluorine-, chlorine-, methyl- or ethyl-substituted cyclopropyl, cyclobutyl, cyclopentyl or cyclohexyl.

3. A herbicidal composition, comprising one or more compounds of claim 1 and one or more extenders and/or surfactants.

4. A method for controlling weeds, comprising the step of allowing an effective amount of the compound of claim 1 to act on the weeds or their habitat.

5. A compound of the formula (IV)

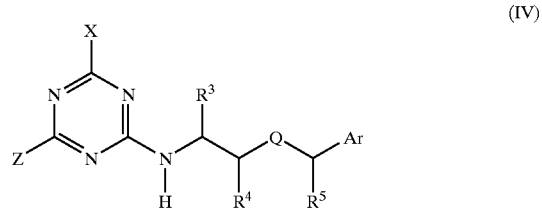

(IV)

wherein

Q, $R^3$, $R^4$, $R^5$, Ar and Z are as defined in claim 1, and

X represents halogen.

* * * * *